(12) United States Patent
Gibson et al.

(10) Patent No.: US 7,622,500 B2
(45) Date of Patent: Nov. 24, 2009

(54) ANTIPARASITIC AGENTS

(75) Inventors: Stephen Paul Gibson, Sandwich (GB); Christelle Lauret, Sandwich (GB)

(73) Assignee: Pfizer Limited, Sandwich, Kent (GB)

( * ) Notice: Subject to any disclaimer, the term of this patent is extended or adjusted under 35 U.S.C. 154(b) by 0 days.

(21) Appl. No.: 12/034,429

(22) Filed: Feb. 20, 2008

(65) Prior Publication Data

US 2008/0200540 A1    Aug. 21, 2008

Related U.S. Application Data

(60) Provisional application No. 60/890,914, filed on Feb. 21, 2007.

(51) Int. Cl.
*A61K 31/343* (2006.01)
*C07D 307/78* (2006.01)

(52) U.S. Cl. ...................... 514/469; 549/469

(58) Field of Classification Search ............ 549/200, 549/429, 456, 462, 469; 514/469
See application file for complete search history.

(56) References Cited

FOREIGN PATENT DOCUMENTS

| EP | 0 953 565 | 3/1999 |
|---|---|---|
| WO | 02/49641 | 6/2002 |
| WO | 02/50052 | 6/2002 |
| WO | 02/060257 | 8/2002 |
| WO | 2005/044784 | 5/2005 |
| WO | 2005/121075 | 12/2005 |
| WO | 2006/043654 | 4/2006 |

OTHER PUBLICATIONS

Stella, Valentino J, Expert Opinion of Therapeutic Patents, Prodrugs as therapeutics, 2004 14(3): 277-280.*
Wolff et al. (Burger's Medicinal Chemistry, 5th Ed., vol. 1, pp. 975-977, 1994).*
Testa, Bernard, Biochemical Pharmacology, Prodrug Research: futile or fertile? 68 (2004) 2097-2106.*
Ettmayer, Peter, Medicinal Chemistry, Lessons Learned from Marketed and Investigational Prodrugs, 47(10) (2004) 2394-2404.*
"Tautomer." Retrieved online via the Internet [Nov. 15, 2008] URL: http://en.wikipedia.org/wiki/Tautomer.*
PCT International Search Report, PCT/IB2008/000362.

* cited by examiner

*Primary Examiner*—Kamal A Saeed
*Assistant Examiner*—Samantha L Shterengarts
(74) *Attorney, Agent, or Firm*—Martha A. Gammill

(57) ABSTRACT

The present invention relates to compounds of the formula (I)

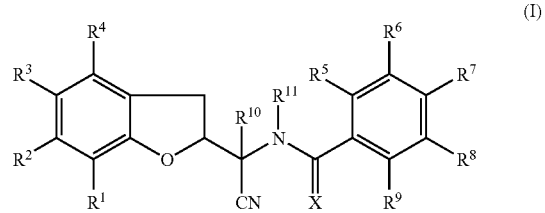

and pharmaceutically acceptable salts thereof, compositions containing such compounds and the uses of such compounds as antiparasitic agents.

24 Claims, No Drawings

ANTIPARASITIC AGENTS

CROSS-REFERENCE TO RELATED APPLICATIONS

This application claims the benefit of priority to U.S. Provisional Application No. 60/890,914 filed Feb. 21, 2007.

BACKGROUND OF THE INVENTION

The present invention relates to pentafluorothiobenzamidoacetonitrile derivatives. The invention also relates to pharmaceutical compositions containing such compounds and their use in treating parasitic infestations.

There is a continuing need to provide new agents for the control of parasitic infestations that present a threat to human and animal health. In particular, new agents are needed to manage endoparasitic infestations in livestock animals due to the increasing prevalence of parasites, and in particular nematodes, that are resistant to many of the agents currently approved for this indication.

European patent application EP-0953565-A2 (Nihon Nohyaku Co. Ltd.) describes a genus of amidoacetonitrile derivatives and reports that these compounds have insecticidal properties. International patent application WO-2002/060257-A1 (Novartis AG) records that the same genus is active against endoparasites such as helminths. Related genera and subgenera are discussed in WO-2002/049641-A2 (Novartis), WO-2002/050052-A1 (Syngenta), WO-2005/044784-A1 (Novartis), WO-2005/121075-A1 (Novartis) and WO-2006/043654 (Nihon). The mechanism by which these agents act has not yet been fully elucidated.

There remains a need for further compounds as alternative or improved therapeutic agents. Preferred compounds should be potent parasiticidal agents while presenting little or no toxicity to the host animal, and should exist in a physical form that is stable, non-hygroscopic and easily formulated. They should have high bioavailability, be metabolically stable and possess favourable pharmacokinetic properties. When intended for use in livestock animals, the compounds should be cleared in such a manner as to minimise withholding times without presenting a risk to the food chain.

SUMMARY OF THE INVENTION

In a first aspect, the present invention provides a compound of the formula

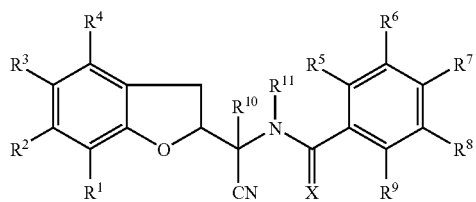

(I)

or a tautomer or prodrug thereof, or a pharmaceutically acceptable salt of said compound, tautomer or prodrug, wherein:

X is O or S;

$R^1$, $R^2$, $R^3$ and $R^4$ are each independently selected from H, halo, CN, $(C_1-C_4)$alkyl optionally substituted by $R^A$, $(C_3-C_6)$cycloalkyl optionally substituted by $R^A$, $(C_1-C_4)$haloalkyl, Ar, $Het^A$, $Het^B$, CHO, C(O)—$(C_1-C_4)$alkyl, C(O)—$(C_1-C_4)$haloalkyl, C(O)Ar, C(O)$Het^A$; C(O)$OR^B$, C(O)$NR^CR^D$, $OR^B$, O—CHO, OC(O)—$(C_1-C_4)$alkyl, OC(O)—$(C_1-C_4)$haloalkyl, OC(O)Ar, OC(O)$Het^A$; OC(O)$OR^E$, OC(O)$NR^CR^D$, $NR^CR^D$, NH—CHO, NH—C(O)—$(C_1-C_4)$alkyl, NH—C(O)—$(C_1-C_4)$haloalkyl, NH—C(O)Ar, NH—C(O)$Het^A$; NH—C(O)$OR^E$, NH—C(O)$NR^CR^D$, NH—S(O)$_2R^E$, NH—S(O)$_2NR^CR^D$, S(O)$_nNR^E$ and S(O)$_2NR^CR^D$, $R^5$, $R^6$, $R^7$, $R^8$ and $R^9$ are each independently selected from H, halo, $(C_1-C_4)$alkyl, $(C_3-C_6)$cycloalkyl, $(C_1-C_4)$haloalkyl, O—$(C_1-C_4)$alkyl, O—$(C_3-C_6)$cycloalkyl, O—$(C_1-C_4)$haloalkyl, $SF_5$, $S(O)_m$—$(C_1-C_4)$alkyl, $S(O)_m$—$(C_3-C_6)$cycloalkyl and $S(O)_m$—$(C_1-C_4)$haloalkyl;

$R^{10}$ is H or $(C_1-C_4)$alkyl;

$R^{11}$ is H or $(C_1-C_4)$alkyl;

$R^A$ is selected from CN, $(C_3-C_6)$cycloalkyl, $OR^B$, $NR^CR^D$, $S(O)_nR^E$, C(O)$OR^B$, C(O)$NR^CR^D$, Ar, $Het^A$ and $Het^B$;

$R^B$ is selected from H and $R^E$;

$R^C$ and $R^D$ are each independently selected from H and $R^E$, or $R^C$ and $R^D$ together with the nitrogen atom to which they are attached form a pyrrolidine, piperidine, piperazine or morpholine ring;

$R^E$ is selected from Ar, $Het^A$, $(C_3-C_6)$cycloalkyl, $(C_1-C_4)$haloalkyl and $(C_1-C_4)$alkyl optionally substituted by $(C_3-C_6)$cycloalkyl, Ar or $Het^A$;

Ar is phenyl optionally substituted with up to three groups independently selected from halo, $(C_1-C_4)$alkyl, OH and O—$(C_1-C_4)$alkyl;

$Het^A$ is a 5- or 6-membered aromatic ring with one heteroatom selected from N, O and S, and optionally one or two further nitrogen atoms, which ring may optionally be substituted with up to three groups independently selected from halo, $(C_1-C_4)$alkyl and O—$(C_1-C_4)$alkyl;

$Het^B$ is a 3-, 4-, 5-, 6- or 7-membered saturated ring with one or two heteroatoms selected from N, O and S, which ring may optionally be substituted with up to three $(C_1-C_4)$alkyl groups;

m is 0, 1 or 2; and n is 0, 1 or 2.

In a further aspect, the present invention provides a compound of the formula (I) or a tautomer or prodrug thereof, or a pharmaceutically acceptable salt of said compound, tautomer or prodrug, for use as a medicament.

In a further aspect, the present invention provides for the use of a compound of the formula (I) or a tautomer or prodrug thereof, or a pharmaceutically acceptable salt of said compound, tautomer or prodrug, for the preparation of a medicament for the treatment of a parasitic infestation in a host animal.

In a further aspect, the present invention provides for a method of treatment of a parasitic infestation in a host animal, comprising treating the host animal with an effective amount of a compound of the formula (I) or a tautomer or prodrug thereof, or a pharmaceutically acceptable salt of said compound, tautomer or prodrug.

In a further aspect, the present invention provides a pharmaceutical composition comprising a compound of the formula (I) or a tautomer or prodrug thereof, or a pharmaceutically acceptable salt of said compound, tautomer or prodrug, and a pharmaceutically acceptable carrier.

DETAILED DESCRIPTION OF THE INVENTION

For the purposes of the present document, the following definitions apply:

"Alkyl" means a saturated monovalent hydrocarbon radical $C_nH_{2n+1}$ which may be linear or branched. $C_1-C_4$ alkyl includes methyl, ethyl, n-propyl, isopropyl (1-methylethyl), n-butyl, sec-butyl (1-methylpropyl), isobutyl (2-methylpropyl) and tert-butyl (1,1-dimethylethyl). "Substituted alkyl" indicates that a hydrogen atom of the alkyl group is replaced by the indicated substituent.

"Cycloalkyl" means a saturated monovalent monocyclic or bridged or fused polycyclic hydrocarbon radical. $C_3$-$C_6$ cycloalkyl includes cyclopropyl, cyclobutyl, cyclopentyl and cyclohexyl. "Substituted cycloalkyl" indicates that a hydrogen atom of the cycloalkyl group is replaced by the indicated substituent.

"Halo" includes fluoro, chloro, bromo or iodo.

"Haloalkyl" means an alkyl group as defined above wherein one or more hydrogen atoms is replaced by a halogen atom selected from fluorine, chlorine, bromine and iodine. When the group contains more than one halogen atom then these atoms may be the same or different. Haloalkyl includes perhaloalkyl, i.e. an alkyl group wherein all the hydrogen atoms are replaced by halogen atoms. $C_1$-$C_4$ haloalkyl includes fluoromethyl, chloromethyl, difluoromethyl, chlorodifluoromethyl, bromodichloromethyl, trifluoromethyl, 2-bromoethyl, 2,2,2-trifluoroethyl, pentafluoroethyl, 3-iodopropyl and 2,2,2-trichloro-1,1-dimethylethyl.

The term "pharmaceutically acceptable" as used in this specification, for example with reference to salts and solvates, includes "veterinarily acceptable" and "agriculturally acceptable".

Specific embodiments of 5- and 6-membered aromatic rings within the definition of $Het^A$ include pyrrolyl, furyl, thienyl, oxazolyl, isoxazolyl, thiazolyl, isothiazolyl, pyrazolyl, imidazolyl, oxadiazolyl, thiadiazolyl, triazolyl, pyridinyl, pyridazinyl, pyrimidinyl, pyrazinyl, pyridin-2-onyl, pyridin-4-onyl, pyran-2-onyl and pyran-4-onyl.

Specific embodiments of 3-, 4-, 5-, 6- and 7-membered saturated rings within the definition of $Het^B$ include aziridinyl, oxiranyl, thiranyl, azetidinyl, oxetanyl, pyrrolidinyl, tetrahydrofuranyl, tetrahydrothienyl, piperidinyl, piperazinyl, morpholinyl and diazepanyl.

The compounds of formula (I) have two asymmetric carbon atoms (chiral centres), labelled 1* and 2* in the structural formula below. Certain embodiments of the substituents $R^1$ to $R^{11}$ may include additional chiral centres. Accordingly, the compounds of formula (I) may exist as optical isomers. The present invention includes individual enantiomers and diastereomers of the compounds of formula (I) and mixtures thereof, including racemates. Where there is an additional chiral centre in a substituent then the invention includes diastereomeric mixtures as well as individual stereoisomers.

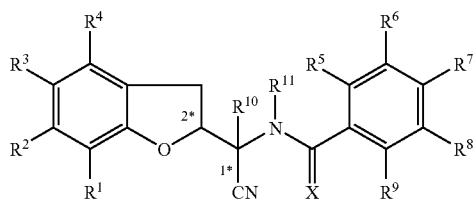

Certain compounds of formula (I) may exist as geometric isomers. The present invention encompasses such compounds in the cis (Z-) or trans (E-) configuration, as well as mixtures of these geometric isomers.

Certain compounds of formula (I) may exist in more than one tautomeric form. The present invention encompasses all such tautomers, as well as mixtures thereof.

The present invention includes all pharmaceutically acceptable isotopically-labelled compounds of formula (I) wherein one or more atoms are replaced by atoms having the same atomic number, but an atomic mass or mass number different from the atomic mass or mass number which predominates in nature.

Examples of isotopes suitable for inclusion in the compounds of the invention include isotopes of hydrogen, such as $^2H$ and $^3H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$.

Certain isotopically-labelled compounds of formula (I), for example, those incorporating a radioactive isotope, are useful in drug and/or substrate tissue distribution studies. The radioactive isotopes tritium, i.e. $^3H$, and carbon-14, i.e. $^{14}C$, are particularly useful for this purpose in view of their ease of incorporation and ready means of detection.

Substitution with heavier isotopes such as deuterium, i.e. $^2H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy.

Isotopically-labeled compounds of formula (I) can generally be prepared by conventional techniques known to those skilled in the art or by processes analogous to those described in the accompanying Examples and Preparations using an appropriate isotopically-labeled reagent in place of the non-labeled reagent previously employed.

Certain compounds of formula (I) which have a basic functional group are able to form addition salts with acids. Certain compounds of formula (I) which have an acidic functional group are able to form salts with suitable bases. Such salts are included within the scope of the present invention to the extent that they are acceptable for veterinary or pharmaceutical use.

Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinafoate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts.

Hemisalts of acids and bases may also be formed, for example, hemisulphate and hemicalcium salts.

For a review on suitable salts, see *Handbook of Pharmaceutical Salts: Properties, Selection, and Use* by Stahl and Wermuth (Wiley-VCH, 2002).

Pharmaceutically acceptable salts of compounds of formula (I) may be prepared by one or more of three methods:
(i) by reacting the compound of formula (I) with the desired acid or base;

(ii) by removing an acid- or base-labile protecting group from a suitable precursor of the compound of formula (I) or by ring-opening a suitable cyclic precursor, for example, a lactone or lactam, using the desired acid or base; or (iii) by converting one salt of the compound of formula (I) to another by reaction with an appropriate acid or base or by means of a suitable ion exchange column.

All three reactions are typically carried out in solution. The resulting salt may precipitate out and be collected by filtration or may be recovered by evaporation of the solvent.

The compounds of formula (I) and their salts may exist in a continuum of solid states ranging from fully amorphous to fully crystalline. The term 'amorphous' refers to a state in which the material lacks long range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterised by a change of state, typically second order ('glass transition'). The term 'crystalline' refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterised by a phase change, typically first order ('melting point').

The compounds of formula (I) and their salts may also exist in unsolvated and solvated forms. The term 'solvate' is used herein to describe a molecular complex comprising the compound of the invention and one or more pharmaceutically acceptable solvent molecules, for example, ethanol. The term 'hydrate' is employed when said solvent is water.

A currently accepted classification system for organic hydrates is one that defines isolated site, channel, or metal-ion coordinated hydrates—see *Polymorphism in Pharmaceutical Solids* by K. R. Morris (Ed. H. G. Brittain, Marcel Dekker, 1995). Isolated site hydrates are ones in which the water molecules are isolated from direct contact with each other by intervening organic molecules. In channel hydrates, the water molecules lie in lattice channels where they are next to other water molecules. In metal-ion coordinated hydrates, the water molecules are bonded to the metal ion.

When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

Pharmaceutically acceptable solvates in accordance with the invention include those wherein the solvent of crystallization may be isotopically substituted, e.g. $D_2O$, $d_6$-acetone, $d_6$-DMSO.

Also included within the scope of the invention are multi-component complexes (other than salts and solvates) wherein the drug and at least one other component are present in stoichiometric or non-stoichiometric amounts. Complexes of this type include clathrates (drug-host inclusion complexes) and co-crystals. The latter are typically defined as crystalline complexes of neutral molecular constituents which are bound together through non-covalent interactions, but could also be a complex of a neutral molecule with a salt. Co-crystals may be prepared by melt crystallisation, by recrystallisation from solvents, or by physically grinding the components together—see Chem Commun, 17, 1889-1896, by O. Almarsson and M. J. Zaworotko (2004). For a general review of multi-component complexes, see J Pharm Sci, 64 (8), 1269-1288, by Haleblian (August 1975).

The compounds of formula (I) and their salts may also exist in a mesomorphic state (mesophase or liquid crystal) when subjected to suitable conditions. The mesomorphic state is intermediate between the true crystalline state and the true liquid state (either melt or solution). Mesomorphism arising as the result of a change in temperature is described as 'thermotropic' and that resulting from the addition of a second component, such as water or another solvent, is described as 'lyotropic'. Compounds that have the potential to form lyotropic mesophases are described as 'amphiphilic' and consist of molecules which possess an ionic (such as $-COO^-Na^+$, $-COO^-K^+$, or $-SO_3^-Na^+$) or non-ionic (such as $-N^-N^+(CH_3)_3$) polar head group. For more information, see *Crystals and the Polarizing Microscope* by N. H. Hartshorne and A. Stuart, 4$^{th}$ Edition (Edward Arnold, 1970).

Hereinafter all references to compounds of formula (I) include references to salts, solvates, multi-component complexes and liquid crystals thereof and to solvates, multi-component complexes and liquid crystals of salts thereof.

In a preferred embodiment of the compounds of formula (I), $R^1$, $R^2$, $R^3$ and $R^4$ are each independently selected from H, F, Cl, Br, CN, $(C_1-C_4)$alkyl, $(C_1-C_4)$haloalkyl and $OR^B$; and $R^B$ is $(C_1-C_4)$alkyl or $(C_1-C_4)$haloalkyl. More preferably, at least one of $R^1$, $R^2$, $R^3$ and $R^4$ is CN and at least two of $R^1$, $R^2$, $R^3$ and $R^4$ are H. More preferably still, one of $R^1$ and $R^4$ is H and the other is selected from H, F, Cl, Br and $CF_3$, and one of $R^2$ and $R^3$ is H and the other is CN.

In another preferred embodiment of the compounds of formula (I), one of one of $R^5$, $R^6$, $R^7$, $R^8$ and $R^9$ is selected from halo, $(C_1-C_4)$haloalkyl, $O-(C_1-C_4)$haloalkyl, $SF_5$ and $S(O)_m-(C_1-C_4)$haloalkyl and the others are H. More preferably one of $R^6$ and $R^7$ is $CF_3$, $OCF_3$, $SF_5$, $SCF_3$ or $S(O)_2CF_3$, and the other is H. Most preferably $R^7$ is $CF_3$, $OCF_3$, $SF_5$, $SCF_3$ or $S(O)_2CF_3$ and $R^7$, $R^8$, $R^{10}$ and $R^{11}$ are H.

In another preferred embodiment of the compounds of formula (I), $R^{10}$ is $(C_1-C_4)$alkyl. More preferably $R^{10}$ is methyl.

In another preferred embodiment of the compounds of formula (I), $R^{11}$ is H. More preferably $R^{11}$ is H and X is O.

Another preferred embodiment of the compounds of formula (I) is a compound of the formula

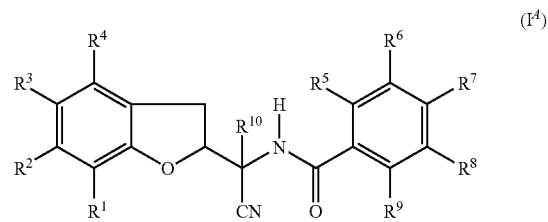

wherein $R^1$, $R^2$, $R^3$ and $R^4$ are each independently selected from H, halo, CN, $(C_1-C_4)$alkyl optionally substituted by $R^A$, $(C_3-C_6)$cycloalkyl optionally substituted by $R^A$, $(C_1-C_4)$haloalkyl, Ar, Het$^A$, Het$^B$, CHO, C(O)—$(C_1-C_4)$alkyl, C(O)—$(C_1-C_4)$haloalkyl, C(O)Ar, C(O)Het$^A$; C(O)OR$^B$, C(O)NR$^C$R$^D$, OR$^B$, O—CHO, OC(O)—$(C_1-C_4)$alkyl, OC(O)—$(C_1-C_4)$haloalkyl, OC(O)Ar, OC(O)Het$^A$; OC(O)OR$^E$, OC(O)NR$^C$R$^D$, NR$^C$R$^D$, NH—CHO, NH—C(O)—$(C_1-C_4)$alkyl, NH—C (O)—($C_1$-$C_4$)haloalkyl, NH—C(O)Ar, NH—C(O)$Het^A$; NH—C(O)$OR^E$, NH—C(O)$NR^CR^D$, NH—S(O)$_2R^E$, NH—S(O)$_2NR^CR^D$, S(O)$_nNR^E$ and S(O)$_2NR^CR^D$, $R^5$, $R^6$, $R^7$, $R^8$ and $R^9$ are each independently selected from H, halo, ($C_1$-$C_4$)alkyl, ($C_3$-$C_6$)cycloalkyl, ($C_1$-$C_4$)haloalkyl, O—($C_1$-$C_4$)alkyl, O—($C_3$-$C_6$)cycloalkyl, O—($C_1$-$C_4$)haloalkyl, $SF_5$, S(O)$_m$—($C_1$-$C_4$)alkyl, S(O)$_m$—($C_3$-$C_6$)cycloalkyl and S(O)$_m$—($C_1$-$C_4$)haloalkyl;

$R^{10}$ is H or ($C_1$-$C_4$)alkyl;

$R^A$ is selected from CN, ($C_3$-$C_6$)cycloalkyl, $OR^B$, $NR^CR^D$, S(O)$_nR^E$, C(O)$OR^B$, C(O)$NR^CR^D$, Ar, $Het^A$ and $Het^B$;

$R^B$ is selected from H and $R^E$;

$R^C$ and $R^D$ are each independently selected from H and $R^E$, or $R^C$ and $R^D$ together with the nitrogen atom to which they are attached form a pyrrolidine, piperidine, piperazine or morpholine ring;

$R^E$ is selected from Ar, $Het^A$, ($C_3$-$C_6$)cycloalkyl, ($C_1$-$C_4$)haloalkyl and ($C_1$-$C_4$)alkyl optionally substituted by ($C_3$-$C_6$)cycloalkyl, Ar or $Het^A$;

Ar is phenyl optionally substituted with up to three groups independently selected from halo, ($C_1$-$C_4$)alkyl, OH and O—($C_1$-$C_4$)alkyl;

$Het^A$ is a 5- or 6-membered aromatic ring with one heteroatom selected from N, O and S, and optionally one or two further nitrogen atoms, which ring may optionally be substituted with up to three groups independently selected from halo, ($C_1$-$C_4$)alkyl and O—($C_1$-$C_4$)alkyl;

$Het^B$ is a 3-, 4-. 5-, 6- or 7-membered saturated ring with one or two heteroatoms selected from N, O and S, which ring may optionally be substituted with up to three ($C_1$-$C_4$)alkyl groups;

m is 0, 1 or 2; and n is 0, 1 or 2.

In a preferred embodiment of the compounds of formula ($I^A$), $R^1$, $R^2$, $R^3$ and $R^4$ are each independently selected from H, F, Cl, Br, CN, ($C_1$-$C_4$)alkyl, ($C_1$-$C_4$)haloalkyl and $OR^B$; and $R^B$ is ($C_1$-$C_4$)alkyl or ($C_1$-$C_4$)haloalkyl. More preferably, at least one of $R^1$, $R^2$, $R^3$ and $R^4$ is CN and at least two of $R^1$, $R^2$, $R^3$ and $R^4$ are H. More preferably still, one of $R^1$ and $R^4$ is H and the other is selected from H, F, Cl, Br and $CF_3$, and one of $R^2$ and $R^3$ is H and the other is CN.

In another preferred embodiment of the compounds of formula ($I^A$), one of one of $R^5$, $R^6$, $R^7$, $R^8$ and $R^9$ is selected from halo, ($C_1$-$C_4$)haloalkyl, O—($C_1$-$C_4$)haloalkyl, $SF_5$ and S(O)$_m$—($C_1$-$C_4$)haloalkyl and the others are H. More preferably one of $R^6$ and $R^7$ is $CF_3$, $OCF_3$, $SF_5$, $SCF_3$ or S(O)$_2CF_3$, and the other is H. Most preferably $R^7$ is $CF_3$, $OCF_3$, $SF_5$, $SCF_3$ or S(O)$_2CF_3$ and $R^7$, $R^8$, $R^{10}$ and $R^{11}$ are H.

In another preferred embodiment of the compounds of formula ($I^A$), $R^{10}$ is ($C_1$-$C_4$)alkyl. More preferably $R^{10}$ is methyl.

Another preferred embodiment of the compounds of formula (I) is a compound of the formula ($I^B$)

wherein $R^1$, $R^2$, $R^3$ and $R^4$ are each independently selected from H, halo, CN, ($C_1$-$C_4$)alkyl optionally substituted by $R^A$, ($C_3$-$C_6$)cycloalkyl optionally substituted by $R^A$, ($C_1$-$C_4$)haloalkyl, Ar, $Het^A$, $Het^B$, CHO, C(O)—($C_1$-$C_4$)alkyl, C(O)—($C_1$-$C_4$)haloalkyl, C(O)Ar, C(O)$Het^A$; C(O)$OR^B$, C(O)$NR^CR^D$, $OR^B$, O—CHO, OC(O)—($C_1$-$C_4$)alkyl, OC(O)—($C_1$-$C_4$)haloalkyl, OC(O)Ar, OC(O)$Het^A$; OC(O)$OR^E$, OC(O)$NR^CR^D$, $NR^CR^D$, NH—CHO, NH—C(O)—($C_1$-$C_4$)alkyl, NH—C(O)—($C_1$-$C_4$)haloalkyl, NH—C(O)Ar, NH—C(O)$Het^A$; NH—C(O)$OR^E$, NH—C(O)$NR^CR^D$, NH—S(O)$_2R^E$, NH—S(O)$_2NR^CR^D$, S(O)$_nNR^E$ and S(O)$_2NR^CR^D$, $R^5$, $R^6$, $R^7$, $R^8$ and $R^9$ are each independently selected from H, halo, ($C_1$-$C_4$)alkyl, ($C_3$-$C_6$)cycloalkyl, ($C_1$-$C_4$)haloalkyl, O—($C_1$-$C_4$)alkyl, O—($C_3$-$C_6$)cycloalkyl, O—($C_1$-$C_4$)haloalkyl, $SF_5$, S(O)$_m$—($C_1$-$C_4$)alkyl, S(O)$_m$—($C_3$-$C_6$)cycloalkyl and S(O)$_m$—($C_1$-$C_4$)haloalkyl;

$R^{10}$ is H or ($C_1$-$C_4$)alkyl;

$R^{11}$ is ($C_1$-$C_4$)alkyl;

$R^A$ is selected from CN, ($C_3$-$C_6$)cycloalkyl, $OR^B$, $NR^CR^D$, S(O)$_nR^E$, C(O)$OR^B$, C(O)$NR^CR^D$, Ar, $Het^A$ and $Het^B$;

$R^B$ is selected from H and $R^E$;

$R^C$ and $R^D$ are each independently selected from H and $R^E$, or $R^C$ and $R^D$ together with the nitrogen atom to which they are attached form a pyrrolidine, piperidine, piperazine or morpholine ring;

$R^E$ is selected from Ar, $Het^A$, ($C_3$-$C_6$)cycloalkyl, ($C_1$-$C_4$)haloalkyl and ($C_1$-$C_4$)alkyl optionally substituted by ($C_3$-$C_6$)cycloalkyl, Ar or $Het^A$;

Ar is phenyl optionally substituted with up to three groups independently selected from halo, ($C_1$-$C_4$)alkyl, OH and O—($C_1$-$C_4$)alkyl;

$Het^A$ is a 5- or 6-membered aromatic ring with one heteroatom selected from N, O and S, and optionally one or two further nitrogen atoms, which ring may optionally be substituted with up to three groups independently selected from halo, ($C_1$-$C_4$)alkyl and O—($C_1$-$C_4$)alkyl;

$Het^B$ is a 3-, 4-. 5-, 6- or 7-membered saturated ring with one or two heteroatoms selected from N, O and S, which ring may optionally be substituted with up to three ($C_1$-$C_4$)alkyl groups;

m is 0, 1 or 2; and n is 0, 1 or 2.

In a preferred embodiment of the compounds of formula ($I^B$), $R^1$, $R^2$, $R^3$ and $R^4$ are each independently selected from H, F, Cl, Br, CN, ($C_1$-$C_4$)alkyl, ($C_1$-$C_4$)haloalkyl and $OR^B$; and $R^B$ is ($C_1$-$C_4$)alkyl or ($C_1$-$C_4$)haloalkyl. More preferably, at least one of $R^1$, $R^2$, $R^3$ and $R^4$ is CN and at least two of $R^1$, $R^2$, $R^3$ and $R^4$ are H. More preferably still, one of $R^1$ and $R^4$ is H and the other is selected from H, F, Cl, Br and $CF_3$, and one of $R^2$ and $R^3$ is H and the other is CN.

In another preferred embodiment of the compounds of formula ($I^B$), one of one of $R^5$, $R^6$, $R^7$, $R^8$ and $R^9$ is selected from halo, ($C_1$-$C_4$)haloalkyl, O—($C_1$-$C_4$)haloalkyl, $SF_5$ and S(O)$_m$—($C_1$-$C_4$)haloalkyl and the others are H. More preferably one of $R^6$ and $R^7$ is $CF_3$, $OCF_3$, $SF_5$, $SCF_3$ or S(O)$_2CF_3$, and the other is H. Most preferably $R^7$ is $CF_3$, $OCF_3$, $SF_5$, $SCF_3$ or S(O)$_2CF_3$ and $R^7$, $R^8$, $R^{10}$ and $R^{11}$ are H.

In another preferred embodiment of the compounds of formula ($I^B$), $R^{10}$ is ($C_1$-$C_4$)alkyl. More preferably $R^{10}$ is methyl.

Another preferred embodiment of the compounds of formula (I) is a compound of the formula

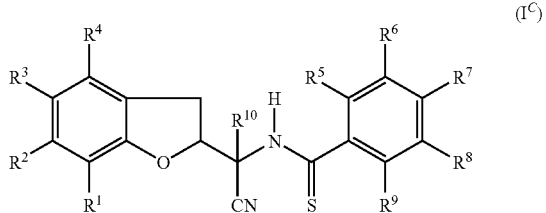

(I^C)

wherein

R^1, R^2, R^3 and R^4 are each independently selected from H, halo, CN, (C_1-C_4)alkyl optionally substituted by R^A, (C_3-C_6) cycloalkyl optionally substituted by R^A, (C_1-C_4)haloalkyl, Ar, Het^A, Het^B, CHO, C(O)—(C_1-C_4)alkyl, C(O)—(C_1-C_4)haloalkyl, C(O)Ar, C(O)Het^A; C(O)OR^B, C(O)NR^CR^D, OR^B, O—CHO, OC(O)—(C_1-C_4)alkyl, OC(O)—(C_1-C_4)haloalkyl, OC(O)Ar, OC(O)Het^A; OC(O)OR^E, OC(O)NR^CR^D, NR^CR^D, NH—CHO, NH—C(O)—(C_1-C_4)alkyl, NH—C(O)—(C_1-C_4)haloalkyl, NH—C(O)Ar, NH—C(O)Het^A; NH—C(O)OR^E, NH—C(O)NR^CR^D, NH—S(O)_2R^E, NH—S(O)_2NR^CR^D, S(O)_nR^E and S(O)_2NR^CR^D, R^5, R^6, R^7, R^8 and R^9 are each independently selected from H, halo, (C_1-C_4)alkyl, (C_3-C_6)cycloalkyl, (C_1-C_4)haloalkyl, O—(C_1-C_4)alkyl, O—(C_3-C_6)cycloalkyl, O—(C_1-C_4)haloalkyl, SF_5, S(O)_m—(C_1-C_4)alkyl, S(O)_m—(C_3-C_6)cycloalkyl and S(O)_m—(C_1-C_4)haloalkyl;

R^10 is H or (C_1-C_4)alkyl;

R^11 is (C_1-C_4)alkyl;

R^A is selected from CN, (C_3-C_6)cycloalkyl, OR^B, NR^CR^D, S(O)_nR^E, C(O)OR^B, C(O)NR^CR^D, Ar, Het^A and Het^B;

R^B is selected from H and R^E;

R^C and R^D are each independently selected from H and R^E, or R^C and R^D together with the nitrogen atom to which they are attached form a pyrrolidine, piperidine, piperazine or morpholine ring;

R^E is selected from Ar, Het^A, (C_3-C_6)cycloalkyl, (C_1-C_4)haloalkyl and (C_1-C_4)alkyl optionally substituted by (C_3-C_6)cycloalkyl, Ar or Het^A;

Ar is phenyl optionally substituted with up to three groups independently selected from halo, (C_1-C_4)alkyl, OH and O—(C_1-C_4)alkyl;

Het^A is a 5- or 6-membered aromatic ring with one heteroatom selected from N, O and S, and optionally one or two further nitrogen atoms, which ring may optionally be substituted with up to three groups independently selected from halo, (C_1-C_4)alkyl and O—(C_1-C_4)alkyl;

Het^B is a 3-, 4-. 5-, 6- or 7-membered saturated ring with one or two heteroatoms selected from N, O and S, which ring may optionally be substituted with up to three (C_1-C_4)alkyl groups;

m is 0, 1 or 2; and n is 0, 1 or 2.

In a preferred embodiment of the compounds of formula (I^C), R^1, R^2, R^3 and R^4 are each independently selected from H, F, Cl, Br, CN, (C_1-C_4)alkyl, (C_1-C_4)haloalkyl and OR^B; and R^B is (C_1-C_4)alkyl or (C_1-C_4)haloalkyl. More preferably, at least one of R^1, R^2, R^3 and R^4 is CN and at least two of R^1, R^2, R^3 and R^4 are H. More preferably still, one of R^1 and R^4 is H and the other is selected from H, F, Cl, Br and CF_3, and one of R^2 and R^3 is H and the other is CN.

In another preferred embodiment of the compounds of formula (I^C), one of one of R^5, R^6, R^7, R^8 and R^9 is selected from halo, (C_1-C_4)haloalkyl, O—(C_1-C_4)haloalkyl, SF_5 and S(O)_m—(C_1-C_4)haloalkyl and the others are H. More preferably one of R^6 and R^7 is CF_3, OCF_3, SF_5, SCF_3 or S(O)_2CF_3, and the other is H. Most preferably R^7 is CF_3, OCF_3, SF_5, SCF_3 or S(O)_2CF_3 and R^7, R^8, R^10 and R^11 are H.

In another preferred embodiment of the compounds of formula (I^C), R^10 is (C_1-C_4)alkyl. More preferably R^10 is methyl.

Another preferred embodiment of the compounds of formula (I) is a compound of the formula

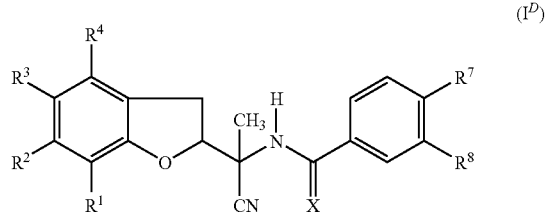

(I^D)

wherein:

X is O or S;

R^1 and R^4 are each independently selected from H, halo, CN, (C_1-C_4)alkyl optionally substituted by R^A, (C_1-C_4)haloalkyl and OR^B;

one of R^2 and R^3 is CN and the other is selected from H and CN;

one of R^7 and R^8 is CF_3, OCF_3, SF_5, SCF_3 or S(O)_2CF_3 and the other is H;

R^A is selected from CN and OR^B;

R^B is selected from H and R^E; and

R^E is selected from (C_1-C_4)haloalkyl and (C_1-C_4)alkyl.

In a preferred embodiment of the compounds of formula (I^D), R^1 and R^4 are each independently selected from H, Cl, Br and CF_3, R^7 is CF_3, OCF_3, SF_5, SCF_3 or S(O)_2CF_3, and R^8 is H. More preferably R^1 is selected from H, Cl, Br and CF_3, R^2 is H, R^3 is CN, and R^4 is H.

In another preferred embodiment of the compounds of formula (I^D), X is O.

In another preferred embodiment of the compounds of formula (I^D), X is O, R^1 and R^4 are each independently selected from H, Cl, Br and CF_3, R^7 is CF_3, OCF_3, SF_5, SCF_3 or S(O)_2CF_3, and R^8 is H. More preferably R^1 is selected from H, Cl, Br and CF_3, R^2 is H, R^3 is CN, and R^4 is H.

Other preferred embodiments of the compounds of formula (I) are compounds of the formula

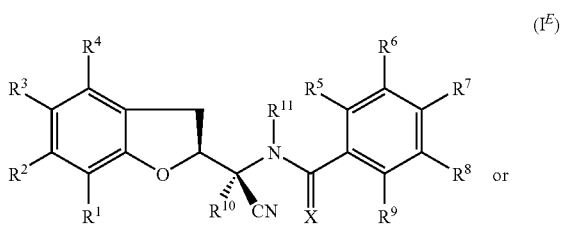

(I^E)

or

-continued

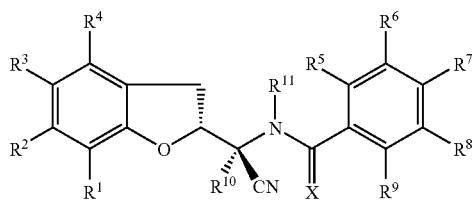

(I^F)

wherein is (C$_1$-C$_4$)alkyl and R$^1$, R$^2$, R$^3$, R$^4$, R$^5$, R$^6$, R$^7$, R$^8$, R$^9$, R$^{10}$ and R$^{11}$ are as defined in any of the foregoing embodiments of the compounds of formulae (I), (I$^A$), (I$^B$), (I$^C$) and (I$^D$), and wherein the stereochemistry depicted is the relative stereochemistry rather than the absolute stereochemistry. It will be recognized that formula (I$^E$) depicts the (R*,R*) diastereomer and formula (I$^F$) depicts the (R*,S*) diastereomer.

Particularly preferred compounds according to formula (I) include:

N-[1-cyano-1-(5-cyano-2,3-dihydro-1-benzofuran-2-yl) ethyl]-4-[(trifluoromethyl)thio]benzamide,
N-{(1R*)-1-cyano-1-[(2R*)-5-cyano-2,3-dihydro-1-benzofuran-2-yl]ethyl}-4-[(trifluoromethyl)thio]benzamide,
N-{(1R)-1-cyano-1-[(2R)-5-cyano-2,3-dihydro-1-benzofuran-2-yl]ethyl}-4-[(trifluoromethyl)thio]benzamide,
N-{(1S)-1-cyano-1-[(2S)-5-cyano-2,3-dihydro-1-benzofuran-2-yl]ethyl}-4-[(trifluoromethyl)thio]benzamide,
N-{(1R*)-1-cyano-1-[(2S*)-5-cyano-2,3-dihydro-1-benzofuran-2-yl]ethyl}-4-[(trifluoromethyl)thio]benzamide,
N-{(1R)-1-cyano-1-[(2S)-5-cyano-2,3-dihydro-1-benzofuran-2-yl]ethyl}-4-[(trifluoromethyl)thio]benzamide,
N-{(1S)-1-cyano-1-[(2R)-5-cyano-2,3-dihydro-1-benzofuran-2-yl]ethyl}-4-[(trifluoromethyl)thio]benzamide,
N-[1-cyano-1-(5-cyano-2,3-dihydro-1-benzofuran-2-yl) ethyl]-4-(trifluoromethoxy)benzamide,
N-{(1R*)-1-cyano-1-[(2R*)-5-cyano-2,3-dihydro-1-benzofuran-2-yl]ethyl}-4-(trifluoromethoxy)benzamide,
N-{(1R)-1-cyano-1-[(2R)-5-cyano-2,3-dihydro-1-benzofuran-2-yl]ethyl}-4-(trifluoromethoxy)benzamide,
N-{(1S)-1-cyano-1-[(2S)-5-cyano-2,3-dihydro-1-benzofuran-2-yl]ethyl}-4-(trifluoromethoxy)benzamide
N-{(1R*)-1-cyano-1-[(2S*)-5-cyano-2,3-dihydro-1-benzofuran-2-yl]ethyl}-4-(trifluoromethoxy)benzamide,
N-{(1R)-1-cyano-1-[(2S)-5-cyano-2,3-dihydro-1-benzofuran-2-yl]ethyl}-4-(trifluoromethoxy)benzamide,
N-{(1S)-1-cyano-1-[(2R)-5-cyano-2,3-dihydro-1-benzofuran-2-yl]ethyl}-4-(trifluoromethoxy)benzamide,
N-[1-(7-chloro-5-cyano-2,3-dihydro-1-benzofuran-2-yl)-1-cyanoethyl]-4-(trifluoromethoxy)benzamide,
N-{(1R*)-1-[(2R*)-7-chloro-5-cyano-2,3-dihydro-1-benzofuran-2-yl)-1-cyanoethyl]-4-(trifluoromethoxy)benzamide,
N-{(1R)-1-[(2R)-7-chloro-5-cyano-2,3-dihydro-1-benzofuran-2-yl)-1-cyanoethyl]-4-(trifluoromethoxy)benzamide,
N-{(1S)-1-[(2S)-7-chloro-5-cyano-2,3-dihydro-1-benzofuran-2-yl)-1-cyanoethyl]-4-(trifluoromethoxy)benzamide,
N-{(1R*)-1-[(2S*)-7-chloro-5-cyano-2,3-dihydro-1-benzofuran-2-yl)-1-cyanoethyl]-4-(trifluoromethoxy)benzamide,
N-{(1R)-1-[(2S)-7-chloro-5-cyano-2,3-dihydro-1-benzofuran-2-yl)-1-cyanoethyl]-4-(trifluoromethoxy)benzamide,
N-{(1S)-1-[(2R)-7-chloro-5-cyano-2,3-dihydro-1-benzofuran-2-yl)-1-cyanoethyl]-4-(trifluoromethoxy)benzamide,
N-[1-(7-chloro-5-cyano-2,3-dihydro-1-benzofuran-2-yl)-1-cyanoethyl]-4-(pentafluorothio)benzamide,
N-{(1R*)-1-[(2R*)-7-chloro-5-cyano-2,3-dihydro-1-benzofuran-2-yl]-1-cyanoethyl}-4-(pentafluorothio)benzamide.
N-{(1R)-1-[(2R)-7-chloro-5-cyano-2,3-dihydro-1-benzofuran-2-yl]-1-cyanoethyl}-4-pentafluorothiobenzamide.
N-{(1S)-1-[(2S)-7-chloro-5-cyano-2,3-dihydro-1-benzofuran-2-yl]-1-cyanoethyl}-4-(pentafluorothio)benzamide,
N-{(1R*)-1-[(2S*)-7-chloro-5-cyano-2,3-dihydro-1-benzofuran-2-yl]-1-cyanoethyl}-4-(pentafluorothio)benzamide,
N-{(1R)-1-[(2S)-7-chloro-5-cyano-2,3-dihydro-1-benzofuran-2-yl]-1-cyanoethyl}-4-(pentafluorothio)benzamide, and
N-{(1S)-1-[(2R)-7-chloro-5-cyano-2,3-dihydro-1-benzofuran-2-yl]-1-cyanoethyl}-4-(pentafluorothio)benzamide.

In a further aspect, the present invention provides processes for the preparation of a compound of formula (I), or a pharmaceutically, veterinarily or agriculturally acceptable salt thereof, or a pharmaceutically, veterinarily or agriculturally acceptable solvate (including hydrate) of either entity, as illustrated below.

It will be apparent to those skilled in the art that sensitive functional groups may need to be protected and deprotected during synthesis of a compound of the invention. This may be achieved by conventional methods, for example as described in "Protective Groups in Organic Synthesis" by T W Greene and P G M Wuts, John Wiley & Sons Inc (1999), and references therein.

The following processes are illustrative of the general synthetic procedures which may be adopted in order to obtain the compounds of the invention.

When one or more of R$^1$, R$^2$, R$^3$, R$^4$, R$^5$, R$^6$, R$^7$, R$^8$, R$^9$, R$^{10}$ and R$^{11}$ contain reactive functional groups then additional protection may be provided according to standard procedures during the synthesis of compounds of formula (I). In the processes described below, for all synthetic precursors used in the synthesis of compounds of formula (I), the definitions of R$^1$, R$^2$, R$^3$, R$^4$, R$^5$, R$^6$, R$^7$, R$^8$, R$^9$, R$^{10}$ and R$^{11}$ wherein R$^1$, R$^2$, R$^3$, R$^4$, R$^5$, R$^6$, R$^7$, R$^8$, R$^9$, R$^{10}$ and R$^{11}$ are as defined for formula (I), are intended to optionally include suitably protected variants, P$^1$, P$^2$, P$^3$, P$^4$, P$^5$, P$^6$, P$^7$, P$^8$, P$^9$, P$^{10}$ and P$^{11}$. Such suitable protecting groups for these functionalities are described in the references listed herein and the use of these protecting groups where needed is specifically intended to fall within the scope of the processes described in the present invention for producing compounds of formula (I) and its precursors. When suitable protecting groups are used, then these will need to be removed to yield compounds of formula (I). Deprotection can be effected according to standard procedures including those described in the references listed herein.

1 Synthesis of Compounds of Formula (I$^A$)

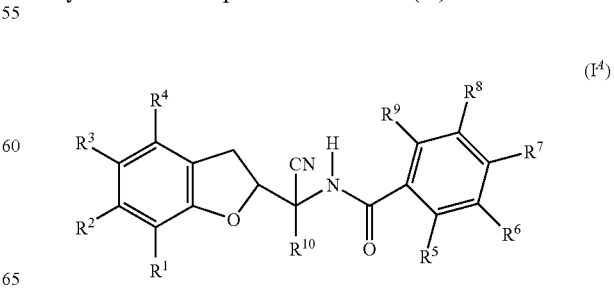

(I$^A$)

1.1 Amide Bond Formation

Compounds of formula (I⁴) wherein $R^1, R^2, R^3, R^4, R^5, R^6, R^7, R^8, R^9$ and $R^{10}$ are as defined for formula (I) may be synthesized by the coupling of amino-nitriles of formula (II), wherein $R^1, R^2, R^3, R^4$, and $R^{10}$ are as defined for formula (I) with acids of formula (III), wherein $R^5, R^6, R^7, R^8$ and $R^9$ are as defined for formula (I), or suitably activated acid derivatives such as acyl halides, esters or anhydrides.

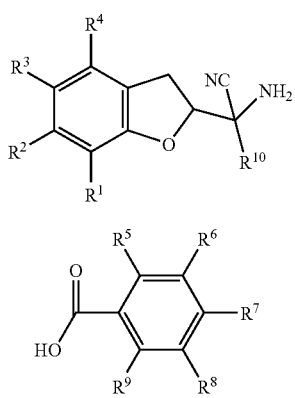

(II)

(III)

Those skilled in the art will recognize that many standard literature reaction conditions may be used to effect such amide bond formation; some of these are reviewed in "Amide bond formation and peptide coupling" C. A. G. N. Montalbetti and V. Falque, Tetrahedron, 2005, 61, 10827-10852.

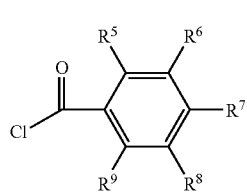

(IV)

For example, amino-nitriles of formula (II) may be reacted with acid chlorides of formula (IV), wherein $R^5, R^6, R^7, R^8$ and $R^9$ are as defined for formula (I), in a dipolar aprotic solvent, such as tetrahydrofuran, in the presence of a base, such as diisopropylethylamine, at reduced temperature, typically 0° C. for 2 to 24 hours.

1.2 Synthesis of Amino-Nitriles of Formula (II)

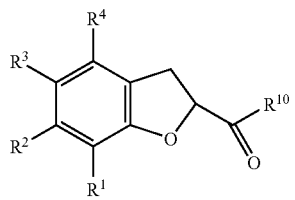

(V)

The amino-nitriles of formula (II) wherein $R^1, R^2, R^3, R^4$, and $R^{10}$ are as defined for formula (I) may be synthesized from ketones of formula (V) using standard literature Strecker synthesis conditions. For example, the ketones of formula (V) may be reacted with ammonium chloride in methanolic ammonia at room temperature for 15-45 minutes followed by the addition of sodium cyanide and continuing the reaction at room temperature for 2-10 hours.

Amino-nitriles of formula (II) wherein $R^1, R^2, R^3, R^4$, and $R^{10}$ are as defined for formula (I) have two stereocentres, one alpha and one beta to the nitrile, provided $R^1, R^2, R^3, R^4$, and $R^{10}$ lack stereocentres. Amino-nitriles of formula (II) with defined stereochemistry alpha to the nitrile may be prepared using a variety of literature asymmetric Strecker syntheses. Some of these procedures are described in Org. Letters, 2000, 2, 6, 867-870; Tetrahedron—Asymmetry 2001, 12, 1147-1150; J. Amer. Chem. Soc. 2003, 125, 5634-5635; J. Amer. Chem. Soc., 1998, 120, 5315-5316; Tetrahedron Letters, 1996, 37, 33, 5839-5840; and Org. Letters, 2004, 5, 26, 5027-5029.

1.3 Acid Chlorides of Formula (IV)

Most of the acid chlorides of formula (IV) may be prepared by standard literature procedures, well known to those skilled in the art, from the acids of formula (III). The acids of formula (III) are generally commercially available or prepared by standard literature procedures well known to those skilled in the art.

The acids of formula (III), wherein one of $R^5, R^6, R^7, R^8$ and $R^9$ is $SF_5$ and the others of $R^5, R^6, R^7, R^8$ and $R^9$ are as defined for formula (I), may be prepared as described in WO-0547240, WO-0547239, JP-2004067525, WO-0397591, U.S. Pat. No. 6,140,528 and W. A. Sheppard, J. Amer. Chem. Soc., 1962, 84, 3064-3072 or by simple modifications of the procedures described therein.

Specifically, 4-pentafluorothiobenzoyl chloride may be prepared according to Scheme A.

Scheme A

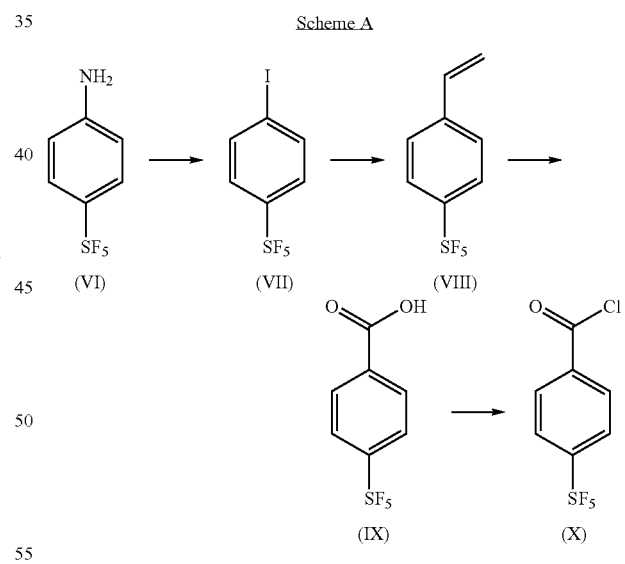

1-Iodo-4-(pentafluorothio)benzene, the compound of formula (VII), may be prepared by the reaction of the diazonium salt formed by the reaction of 4-(pentafluorothio)aniline with sodium nitrite in aqueous hydrochloric acid, with potassium iodide. The diazonium salt is preferably formed at 0° C.; the subsequent iodination may take place at room temperature over a period of 18-60 hours. The alkene of formula (VIII) may be prepared by reaction of the iodo compound of formula (VII) with tributyl(vinyl)tin using a tetrakis(triphenylphosphine)palladium(0) catalyst in a polar solvent, such as N,N-dimethyl formamide at 100° C., under nitrogen, for 1-5 hours, typically 1.5 hours. The acid of formula (IX) may be prepared by oxidation of the alkene, of formula (VIII) using, for example, sodium periodate in an acetonitrile/carbon tetrachloride/water solvent mix in the presence of a ruthenium (III) chloride hydrate catalyst, under an inert atmosphere, at room temperature for 1-20 hours. The acid chloride of formula (X) may be prepared from the acid of formula (XV) using literature procedures well known to those skilled in the art, such as for example heating with excess thionyl chloride at 65° C. for 2-4 hours.

The acid of formula (IX) may be prepared directly from the compound of formula (VII) by reaction of carbon dioxide with an organometallic species generated from (VII); for example using isopropyl magnesium chloride in an anhydrous aprotic solvent such as tetrahydrofuran.

Compounds of formula (IX) and (X) may also be obtained commercially.

1.4 Synthesis of the Ketones of Formula (V)

Ketones of formula (V), wherein $R^1$, $R^2$, $R^3$, $R^4$, and $R^{10}$ are as defined for formula (I), may be prepared as shown in Scheme B.

Acids of formula (XII) may also be available commercially or prepared according to standard literature procedures. Such acids may be taken through the rest of the reactions in Scheme B.

Alternatively, ketones of formula (V), wherein $R^1$, $R^2$, $R^3$, $R^4$, and $R^{10}$ are as defined for formula (I), may be prepared as shown in Scheme C.

Scheme C

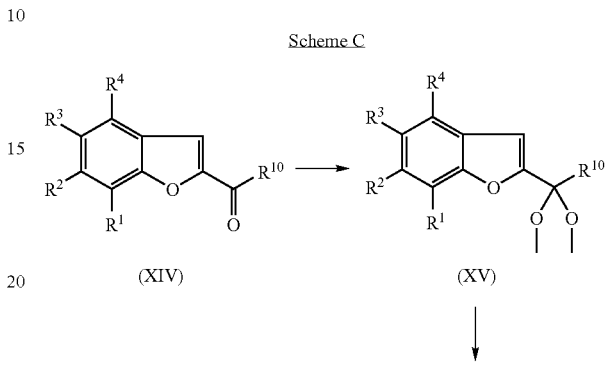

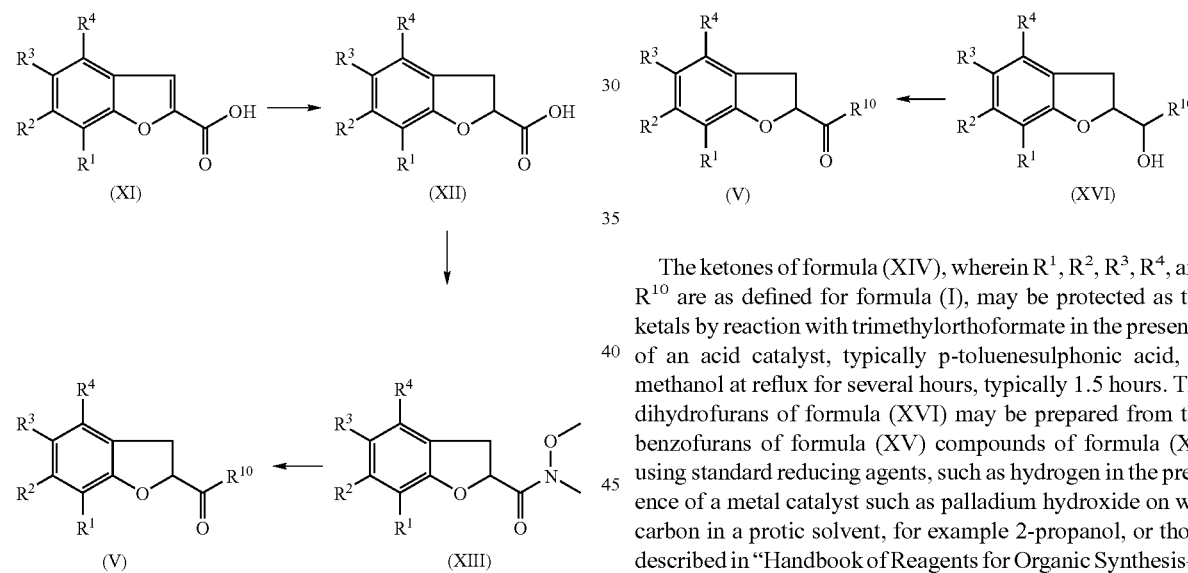

Dihydrofurans of formula (XII), wherein $R^1$, $R^2$, $R^3$ and $R^4$ are as defined for formula (I), may be prepared from the compounds of formula (XI) using standard reducing agents, such as hydrogen in the presence of a metal catalyst such as palladium hydroxide on carbon in a protic solvent, for example acetic acid, or those described in "Handbook of Reagents for Organic Synthesis—Oxidising and Reducing Agents" edited by S. D. Burke and R. L. Danheiser. The methoxyamides of formula (XIII) may be prepared by the coupling of the acids of formula (XII) with N,O-dimethyl hydroxylamine hydrochloride in the presence of 1,1-carbonyldiimidazole in an anhydrous aprotic solvent, such as dichloromethane, for 1-72 hours. The ketones of formula (V) can be prepared by the reaction of the methoxyamides of formula (XIII) with organometallic reagents, such as Grignard reagents, in an aprotic solvent typically tetrahydrofuran at reduced temperature, normally 0° C. in an inert atmosphere.

The ketones of formula (XIV), wherein $R^1$, $R^2$, $R^3$, $R^4$, and $R^{10}$ are as defined for formula (I), may be protected as the ketals by reaction with trimethylorthoformate in the presence of an acid catalyst, typically p-toluenesulphonic acid, in methanol at reflux for several hours, typically 1.5 hours. The dihydrofurans of formula (XVI) may be prepared from the benzofurans of formula (XV) compounds of formula (XI) using standard reducing agents, such as hydrogen in the presence of a metal catalyst such as palladium hydroxide on wet carbon in a protic solvent, for example 2-propanol, or those described in "Handbook of Reagents for Organic Synthesis—Oxidising and Reducing Agents" edited by S. D. Burke and R. L. Danheiser. Using the conditions described above, deprotection of the ketal occurs and the ketone is reduced to the secondary alcohol. Oxidation to the ketones of formula (V) may be effected using standard oxidising agents, such as manganese dioxide in cyclohexane or those described in "Handbook of Reagents for Organic Synthesis—Oxidising and Reducing Agents" edited by S. D. Burke and R. L. Danheiser.

The compounds of formula (V), wherein $R^{10}$=$CH_3$ and $R^1$, $R^2$, $R^3$ and $R^4$ are as defined for formula (I) may be prepared from the acid chlorides of formula (XVII) by reaction with methylmagnesium bromide in the presence of iron acetylacetonate, in an anhydrous aprotic solvent, such as tetrahydrofuran, at reduced temperature, normally −78° C.

In particular, the ketones of formula (XXI) may be prepared as shown in Scheme D.

Scheme D

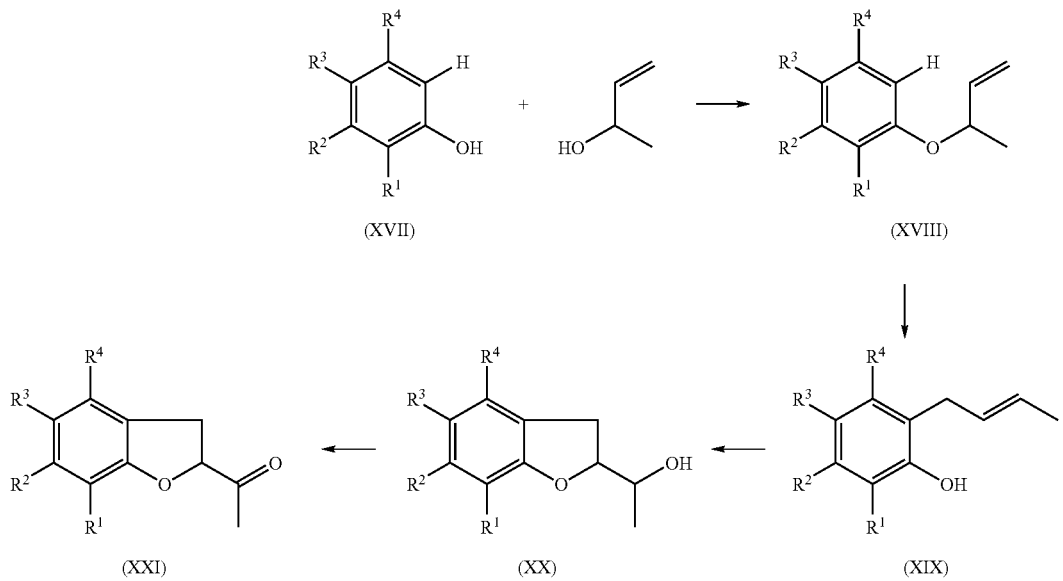

The compounds of formula (XVIII), wherein $R^1$, $R^2$, $R^3$, and $R^4$ are as defined for formula (I) may be prepared by the addition of diisopropyl azodicarboxylate to the phenols of formula (XVII) and but-3-en-2-ol in the presence of triphenylphosphine in a suitable solvent, typically tetrahydrofuran, ensuring the temperature does not rise above 20° C. during the addition. The reaction is then stirred at room temperature for an extended period of time, typically 18 hours. The compound of formula (XIX) may be prepared from the compound of formula (XVIII) by heating for a period of time, 15-60 minutes, in a high boiling point solvent typically at 250° C., such as N,N-diethylaniline, using, for example, a 300 W microwave oven. The compounds of formula (XIX) are oxidized to (XX) using 3-chloroperbenzoic acid in an aprotic solvent, such as dichloromethane, under an inert atmosphere, at reduced temperature, typically 0° C., overnight. The ketones of formula (XXI) may be prepared from the alcohols of formula (XX) using standard oxidizing agents, such as Dess-Martin periodinane or those described in "Handbook of Reagents for Organic Synthesis—Oxidising and Reducing Agents" edited by S. D. Burke and R. L. Danheiser.

2 Synthesis of Compounds of Formula ($I^B$)

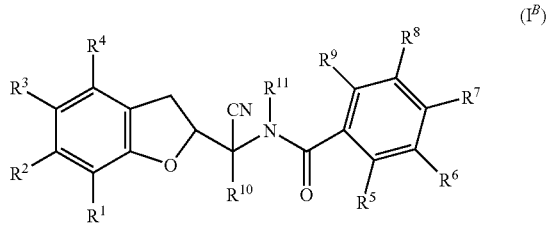

Compounds of formula ($I^B$), wherein $R^1$, $R^2$, $R^3$, $R^4$, $R^5$, $R^6$, $R^7$, $R^8$, $R^9$ and $R^{10}$ are defined as for compounds of formula (I) and $R^{11}$ is $C_1$-$C_4$ alkyl may be prepared by the N-alkylation of compounds of formula ($I^A$) using standard literature procedures well known to those skilled in the art. For example, the anion from compounds of formula ($I^A$) may be prepared in situ by the addition of sodium hydride, or other strong base, in a dipolar aprotic solvent such as tetrahydrofuran at reduced temperature, normally 0° C. The N-alkylated amides of formula ($I^B$) may be prepared by reaction of the anion with compounds of formula $R^{11}$—Y, wherein Y is a suitable leaving group, including but not restricted to—halo, such as chloride, bromide or iodide, methanesulfonate (mesylate), and toluenesulfonate (tosylate) at room temperature for several hours, typically 16 hours.

3 Synthesis of Compounds of Formula ($I^C$)

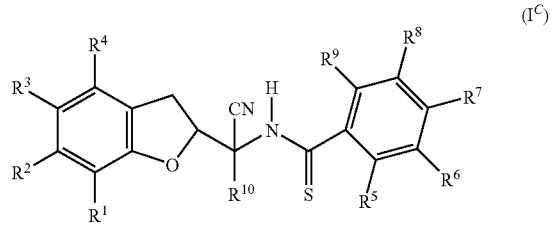

Compounds of formula ($I^C$), wherein $R^1$, $R^2$, $R^3$, $R^4$, $R^5$, $R^6$, $R^7$, $R^8$, $R^9$ and $R^{10}$ are defined as for compounds of formula (I), may be prepared from compounds of formula ($I^A$) using standard literature conditions for converting amides to thioamides. For example, by refluxing with Lawesson's reagent for several hours, typically 16 hours, in a suitable solvent, typically tetrahydrofuran, 5 Functional Group Interconversions.

The substituents, $R^1$, $R^2$, $R^3$ and $R^4$, wherein as defined for compounds of formula (I), in compounds of formula ($I^A$) or compounds of formula (V), may be converted, where chemically feasible, to other substituents, $R^1$, $R^2$, $R^3$ and $R^4$ as defined for compounds of formula ($I^A$). For example, compounds of formula ($I^A$) or (V), wherein one or more of $R^1$, $R^2$, $R^3$ and $R^4$ is $NH_2$, which may be obtained by reduction of the corresponding nitro-substituted compound using standard reducing agents such as those described in "Handbook of Reagents for Organic Synthesis—Oxidising and Reducing Agents" edited by S. D. Burke and R. L. Danheiser, may be mono/bis alkylated, mono/bis sulphonylated or acylated using standard literature conditions.

Compounds of formula ($I^4$) or compounds of formula (V), wherein one of $R^1$, $R^2$, $R^3$ and $R^4$ is halo, particularly bromo, are particularly useful intermediates for making other compounds of formula ($I^4$) or compounds of formula (V). Such bromo compounds may undergo Suzuki couplings with substituted boronic acids or esters in the presence of a palladium (0) or palladium(II) catalyst to give compounds of formula ($I^4$) or compounds of formula (V), wherein one of $R^1$, $R^2$, $R^3$ and $R^4$ is alkyl, or cycloalkyl, or cycloalkylalkyl, or aryl, or arylalkyl. Esters may be obtained from such bromo compounds by the Pd-catalysed carbonylation using carbon monoxide in the presence of alcohols in a solvent such as N,N-dimethyl formamide. These esters may be converted to acids and amides using literature procedures well known to those skilled in the art. These bromo compounds may also undergo a variety of organometallic coupling reactions. For these reactions, other sensitive functional groups elsewhere in the molecule may require appropriate protection. For example, lithiation using butyl lithium in aprotic solvents, such as tetrahydrofuran, in an inert atmosphere, gives intermediate aryl lithium species which may be reacted with dialkyl sulfides to give alkylthio derivatives. These are readily oxidised to sulfoxides and sulfones using standard oxidising agents, such as those described in "Handbook of Reagents for Organic Synthesis—Oxidising and Reducing Agents" edited by S. D. Burke and R. L. Danheiser.

These aryl lithium species may be reacted with chloroformate esters to give compounds of formula ($I^4$) or compounds of formula (V), wherein one of $R^1$, $R^2$, $R^3$ and $R^4$ is —COO (alkyl).

The bromo compounds may also undergo Stille, Tebbe, Buchwald and Heck couplings according to procedures described in the literature.

In particular, compounds of formula (V) wherein $R^3$=iodo may be converted to compounds of formula (V), wherein $R^3$ is cyano, by reaction with cuprous cyanide, in the presence of tetrabutylammonium bromide in water using a 100 W microwave oven to heat the reaction at temperatures ranging from 140°-180° C. for a few minutes, typically no longer than 3 minutes. Compounds of formula (V), wherein $R^3$ is bromo (or chloro) may be prepared from the corresponding iodo compound by sonicating with nickel bromide (or chloride) in DMF for 15-45 minutes, typically 20 minutes, followed heating in a 100 W microwave oven at 170° C. for a few minutes, typically 5 minutes. Specifically, 5-iodo-2,3-dihydro-1-benzofuran-2-carboxylic acid may be prepared from 2,3-dihydro-1-benzofuran-2-carboxylic acid by iodination with benzyltrimethylammonium dichloroiodate in the presence of zinc chloride in a suitable solvent, typically acetic acid, at room temperature for 30-50 hours.

It will also be appreciated by persons skilled in the art that, within certain of the processes described, the order of the synthetic steps employed may be varied and will depend inter alia on factors such as the nature of other functional groups present in a particular substrate, the availability of key intermediates, and the protecting group strategy (if any) to be adopted. Clearly, such factors will also influence the choice of reagent for use in the said synthetic steps.

The skilled person will appreciate that the compounds of the invention could be made by methods other than those herein described, by adaptation of the methods herein described and/or adaptation of methods known in the art, for example the art described herein, or using standard textbooks such as "Comprehensive Organic Transformations—A Guide to Functional Group Transformations", R C Larock, Wiley-VCH (1999 or later editions).

It is to be understood that the synthetic transformation methods mentioned herein are exemplary only and they may be carried out in various different sequences in order that the desired compounds can be efficiently assembled. The skilled chemist will exercise his judgment and skill as to the most efficient sequence of reactions for synthesis of a given target compound.

The compounds of formula (I) have antiparasitic activity and so are useful in the control of parasitic infestations in host animals.

The parasite may be an endoparasite, such as a helminth, or an ectoparasite, such as an arthropod.

Examples of helminths include parasites of the phylum Platyhelminthes (such as cestodes and trematodes; e.g. *Fasciola* spp.; *Fascioloides* spp.; *Paramphistomum* spp.; *Dicrocoelium* spp.; *Eurytrema* spp.; *Ophisthorchis* spp.; *Fasciolopsis* spp.; *Echinostoma* spp.; *Paragonimus* spp.) and the phylum Nematoda (such as filarial, intestinal and tissue nematodes; e.g. *Haemonchus* spp.; *Ostertagia* spp.; *Cooperia* spp.; *Oesphagastomum* spp.; *Nematodirus* spp.; *Dictyocaulus* spp.; *Trichuris* spp.; *Toxocara* spp.; *Toxascaris* spp.; *Trichinella* spp.; *Dirofilaria* spp.; *Ancyclostoma* spp.; *Necator* spp.; *Strongyloides* spp.; *Capillaria* spp.; *Ascaris* spp.; *Enterobius* spp.; and *Trichostrongylus* spp.).

Examples of arthropods include Acarina, including ticks (e.g. *Ixodes* spp., *Boophilus* spp. e.g. *Boophilus microplus, Amblyomma* spp., *Hyalomma* spp., *Rhipicephalus* spp. e.g. *Rhipicephalus appendiculatus, Haemaphysalis* spp., *Dermacentor* spp., *Ornithodorus* spp. (e.g. *Ornithodorus moubata*)), mites (e.g. *Damalinia* spp., *Dermanyssus gallinae, Sarcoptes* spp. e.g. *Sarcoptes scabiei, Psoroptes* spp., *Chorioptes* spp., *Demodex* spp., *Eutrombicula* spp.); Diptera (e.g. *Aedes* spp., *Anopheles* spp., *Muscidae* spp. e.g. *Stomoxys calcitrans* and *Haematobia irritans, Hypoderma* spp., *Gastrophilus* spp., *Simulium* spp.); Hemiptera (e.g. *Triatoma* spp.); Phthiraptera (e.g. *Damalinia* spp., *Linognathus* spp.); Siphonaptera (e.g. *Ctenocephalides* spp.); Dictyoptera (e.g. *Periplaneta* spp., *Blatella* spp.) and Hymenoptera (e.g. *Monomorium pharaonis*).

The compounds of formula (I) are particularly useful for the control of helminth infestations.

The host animal may be a mammal or a non-mammal, such as a bird or a fish. Where the host animal is a mammal, it may be a human or non-human mammal. Non-human mammals include livestock animals and companion animals, such as cattle, sheep, goats, equines, swine, dogs and cats.

The compounds of formula (I) may be administered by any suitable route. Examples of suitable routes of administration include oral, topical and parenteral administration. The choice of the route will depend on the species of the host animal and the nature of the parasitic infestation. For example, oral administration might be preferred in the case of a human or companion animal host, or for the treatment of endoparasites, while topical administration might be more convenient for treating large numbers of livestock animals such as a herd of cattle.

The compounds of formula (I) may be administered alone or in a formulation appropriate to the specific use envisaged. Generally, they will be administered as a formulation in association with one or more pharmaceutically acceptable excipients. The term "excipient" is used herein to describe any ingredient other than the active components. The choice of excipient will to a large extent depend on factors such as the particular mode of administration, the effect of the excipient on solubility and stability, and the nature of the dosage form.

The compounds of formula (I) may be administered as crystalline or amorphous products, for example, spray-dried dispersions or as produced by melt-extrusion or nano-milling. They may be obtained, for example, as solid plugs, powders, or films (for example, rapid dissolving or mucoadhesive films) by methods such as precipitation, crystallization, freeze drying, or spray drying, or evaporative drying. Microwave or radio frequency drying may be used for this purpose.

The methods by which the compounds of formula (I) may be administered include oral administration by capsule, bolus, tablet, powders, lozenges, chews, multi and nanoparticulates, gels, solid solution, films, sprays, or liquid formulation. Liquid forms include suspensions, solutions, syrups, drenches and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet. Oral drenches are commonly prepared by dissolving or suspending the active ingredient in a suitable medium.

Thus compositions useful for oral administration may be prepared by mixing the active ingredient with a suitable finely divided diluent and/or disintegrating agent and/or binder, and/or lubricant etc. Other possible ingredients include antioxidants, colorants, flavoring agents, preservatives and taste-masking agents.

For oral dosage forms, depending on dose, the drug may make up from 1 wt % to 80 wt % of the dosage form, more typically from 5 wt % to 60 wt % of the dosage form. Examples of suitable disintegrants for use herein include sodium starch glycolate, sodium carboxymethyl cellulose, calcium carboxymethyl cellulose, croscarmellose sodium, crospovidone, polyvinylpyrrolidone, methyl cellulose, lower alkyl-substituted hydroxypropyl cellulose, starch, pregelatinised starch and sodium alginate. Generally, the disintegrant will comprise from 1 wt % to 25 wt %, preferably from 5 wt % to 20 wt % of the dosage form.

Binders are generally used to impart cohesive qualities to a tablet formulation. Examples of suitable binders for use herein include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Examples of diluents include lactose (monohydrate, spray-dried monohydrate, anhydrous and the like), mannitol, xylitol, dextrose, sucrose, sorbitol, microcrystalline cellulose, starch and dibasic calcium phosphate dihydrate.

Oral formulations may also optionally comprise surface active agents, such as sodium lauryl sulfate and polysorbate 80, and glidants such as silicon dioxide and talc. When present, surface active agents may comprise from 0.2 wt % to 5 wt % of the tablet, and glidants may comprise from 0.2 wt % to 1 wt % of the tablet.

Lubricants include magnesium stearate, calcium stearate, zinc stearate, sodium stearyl fumarate, and mixtures of magnesium stearate with sodium lauryl sulphate. Lubricants generally comprise from 0.25 wt % to 10 wt %, preferably from 0.5 wt % to 3 wt % of the tablet.

Exemplary tablets contain up to about 80% drug, from about 10 wt % to about 90 wt % binder, from about 0 wt % to about 85 wt % diluent, from about 2 wt % to about 10 wt % disintegrant, and from about 0.25 wt % to about 10 wt % lubricant.

The formulation of tablets is discussed in "Pharmaceutical Dosage Forms: Tablets, Vol. 1", by H. Lieberman and L. Lachman, Marcel Dekker, N.Y., N.Y., 1980 (ISBN 0-8247-6918-X).

The compounds of formula (I) may be administered topically to the skin, that is dermally or transdermally. The compounds may also be administered via the mucosa or mucous membranes. Typical formulations for this purpose include pour-on, spot-on, dip, spray, mousse, shampoo, powder formulation, gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, J Pharm Sci, 88 (10), 955-958 by Finnin and Morgan (October 1999). Pour-on or spot-on formulations may be prepared by dissolving the active ingredient in an acceptable liquid carrier vehicle such as butyl digol, liquid paraffin or a non-volatile ester, optionally with the addition of a volatile component such as propan-2-ol. Alternatively, pour-on, spot-on or spray formulations can be prepared by encapsulation, to leave a residue of active agent on the surface of the animal.

Injectable formulations may be prepared in the form of a sterile solution which may contain other substances, for example enough salts or glucose to make the solution isotonic with blood. Acceptable liquid carriers include vegetable oils such as sesame oil, glycerides such as triacetin, esters such as benzyl benzoate, isopropyl myristate and fatty acid derivatives of propylene glycol, as well as organic solvents such as pyrrolidin-2-one and glycerol formal. The formulations are prepared by dissolving or suspending the active ingredient in the liquid carrier such that the final formulation contains from 0.01 to 10% by weight of the active ingredient. These formulations may be self-preserving, self-sterilizing or may be non-sterile to which preservatives may be optionally added.

Equally suitably the compounds of formula (I) can be administered parenterally, or by injection directly into the blood stream, muscle or into an internal organ. Suitable routes for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques. Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as powdered a dried form to be used in conjunction with a suitable vehicle such as sterile, pyrogen-free water. The preparation of parenteral formulations under sterile conditions, for example, by lyophilisation, may readily be accomplished using standard pharmaceutical techniques well known to those skilled in the art. The solubility of compounds of formula (I) used in the preparation of parenteral solutions may be increased by the use of appropriate formulation techniques, such as the incorporation of solubility-enhancing agents.

Such formulations are prepared in a conventional manner in accordance with standard medicinal or veterinary practice.

These formulations will vary with regard to the weight of active compound contained therein, depending on the species of host animal to be treated, the severity and type of infection and the body weight of the host. For parenteral, topical and oral administration, typical dose ranges of the active ingredient are 0.01 to 100 mg per kg of body weight of the animal. Preferably the range is 0.1 to 10 mg per kg.

Formulations may be immediate release or be designed to have a controlled or modified release profile. Modified release formulations include those formulations which have a delayed-, sustained-, pulsed-, targeted, or programmed release. Suitable modified release formulations for the purposes of the invention are described in U.S. Pat. No. 6,106,864. Details of other suitable release technologies such as high energy dispersions and osmotic and coated particles are to be found in Verma et al, Pharmaceutical Technology Online, 25(2), 1-14 (2001). The use of chewing gum to achieve controlled release is described in WO 00/35298. Alternatively, compounds of the invention may be formulated as a solid, semi-solid, or thixotropic liquid for administration as an implanted depot providing modified release of the active compound. Examples of such formulations include drug-coated stents and PGLA microspheres.

As an alternative the compounds of formula (I) may be administered to a non-human animal with the feedstuff and for this purpose a concentrated feed additive or premix may be prepared for mixing with the normal animal feed.

The compounds of formula (I) may advantageously be used in combination with one or more further therapeutic agents, including, but not limited to, further antiparasitic agents.

Examples of antiparasitic agents that may be used in combination with the compounds of formula (I) include anthelmintic agents, fasciolicides and ectoparasiticides.

In one embodiment of the invention, the compounds of formula (I) are used in combination with a second anthelmintic agent. Such a combination may reduce the likelihood of resistance developing. Suitable further anthelmintic agents include:
  the macrocyclic lactone class of compounds (such as ivermectin, avermectin, abamectin, emamectin, eprinomectin, doramectin, selamectin, moxidectin, nemadectin, milbemycin and milbemycin derivatives such as those described in EP-357460, EP-444964 and EP-594291, and semisynthetic and biosynthetic avermectin/milbemycin derivatives such as those described in U.S. Pat. No. 5,015,630, WO-9415944 and WO-9522552);
  benzimidazoles (such as albendazole, cambendazole, fenbendazole, flubendazole, mebendazole, oxfendazole, oxibendazole and parbendazole);
  imidazothiazoles and tetrahydropyrimidines (such as tetramisole, levamisole, pyrantel pamoate, oxantel or morantel);
  derivatives and analogues of the paraherquamide/marcfortine class of anthelmintic agents, particularly 2-desoxo-paraherquamide;
  nitroscanate;
  antiparasitic oxazolines (such as those disclosed in U.S. Pat. No. 5,478,855, U.S. Pat. No. 4,639,771 and DE-19520936);
  derivatives and analogues of the general class of dioxomorpholine antiparasitic agents as described in WO-9615121; and
  cyclic depsipeptides (such as those described in WO-9611945, WO-9319053, WO-9325543, EP-626375, EP-382173, WO-9419334, EP-382173, and EP-503538, and particularly emodepside).

In a preferred embodiment, the compounds of formula (I) are used in combination with a macrocyclic lactone anthelmintic agent selected from ivermectin, avermectin, abamectin, emamectin, eprinomectin, doramectin, selamectin, moxidectin, nemadectin and milbemycin oxime.

In another preferred embodiment, the compounds of formula (I) are used in combination with a benzimidazole anthelmintic agent selected from albendazole, cambendazole, fenbendazole, flubendazole, mebendazole, oxfendazole, oxibendazole and parbendazole.

In another preferred embodiment, the compounds of formula (I) are used in combination with an anthelmintic agent selected from tetramisole, levamisole, pyrantel pamoate, oxantel and morantel.

In another embodiment of the invention, the compounds of formula (I) are used in combination with a flukicide, for example a fasciolicide. Suitable agents include closantel, triclabendazole, clorsulon, rafoxanide, niclosamide, praziquantel and epsiprantel.

In another embodiment of the invention, the compounds of formula (I) are used in combination with an ectoparasiticidal agent. Suitable agents include:
  aryl pyrazoles (such as fipronil);
  pyrethroids;
  organophosphates;
  insect growth regulators (such as lufenuron);
  ecdysone agonists (such as tebufenozide and the like);
  spinosyns (such as Spinosad), and
  neonicotinoids (such as imidacloprid and the like).

When the compounds of formula (I) are used to treat a parasitic infestation in a livestock animal then they may be used in combination with any of the agents commonly known in the art to be useful as feed additives for such livestock animals, and which are described in such manuals as "2006 Feed Additive Companion" and "Handbook of Feed Additives 2006". Suitable agents include:
  polyether ionophores (such as lasalocid, monensin, salinomycin, narasin and laidlomycin);
  antibiotics (such as the tetracyclines, bacitracin, tylosin, tiamulin, lincomycin, virginiamycin, quinolone antibacterials and carbadox);
  steroid derivatives (such as melengesterol acetate);
  agents for the prevention or treatment of sub-acute rumen acidosis (such as sodium bicarbonate, acarbose and other amylase or glucosidase inhibitors);
  carcass quality/anabolic agents (such as beta adrenergic ligands, including ractopamine, salbutamol and almeterol); and
  other supplements (such as enzymes, minerals and vitamins).

The two components may be administered simultaneously, sequentially or separately. Where the two components are administered sequentially or separately then they may both be given by the same route, or they may be administered by different routes.

As used herein, simultaneous administration means the administration of both components to the host animal in a single action, which requires the two components to be incorporated into a single dosage unit, such as a single tablet or a single pour-on solution.

Sequential administration means the administration of each component is a separate action, but the two actions are linked. For example, administering a tablet comprising one component and a second tablet comprising the second component is considered to be sequential administration, even if the two tablets are given to the host animal at the same time.

Separate administration refers to the administration of each component independently of the other.

For convenience, simultaneous administration may be preferable.

The two components may be presented in kit form. Such a kit comprises two or more separate pharmaceutical compositions, at least one of which contains a compound of formula (I) and one contains a further antiparasitic agent, and means for separately retaining said compositions, such as a container, divided bottle, or divided foil packet. An example of such a kit is the familiar blister pack used for the packaging of tablets, capsules and the like.

The kit is particularly suitable for administering different dosage forms, for example, oral and parenteral, for administering the separate compositions at different dosage intervals, or for titrating the separate compositions against one another. To assist compliance, the kit typically comprises directions for administration and may be provided with a so-called memory aid.

EXAMPLES

The following Examples illustrate the preparation of compounds of the formula (I).

In the following experimental details, nuclear magnetic resonance (N.m.r.) spectral data were obtained using Varian Inova 300, Varian Inova 400, Varian Mercury 400, Varian Unityplus 400, Bruker AC 300 MHz, Bruker AM 250 MHz or Varian T60 MHz spectrometers, the observed chemical shifts being consistent with the proposed structures. N.m.r. chemical shifts are quoted in p.p.m downfield from tetramethylsilane. In the following Examples, where an Example is indicated as being a mixture of diastereoisomers, then the n.m.r. integrals shown refer to the relative ratio of integrals for the quoted chemical shift. Mass spectral data were obtained on a Finnigan ThermoQuest Aqa, a Waters micromass ZQ, or a Hewlett Packard GCMS System Model 5971 spectrometer. The calculated and observed ions quoted refer to the isotopic composition of lowest mass. HPLC means high performance liquid chromatography. Room temperature means 20 to 25° C.

When the source of a simple precursor is unspecified these compounds may be obtained from commercial suppliers or according to literature procedures. The following is a list of commercial suppliers for such compounds:

Sigma-Aldrich, P O Box 14508, St. Louis, Mo., 63178, USA

Fluorochem Ltd., Wesley Street, Old Glossop, Derbyshire, SK13 7RY, UK

Alfa Aesar, 26 Parkridge Road, Ward Hill, Mass., 01835, USA

Apollo Scientific Ltd., Whitefield Rd., Bredbury, Stockport, Cheshire, SK6 2QR, UK Fluka Chemie GmbH, Industriestrasse 25, P.O. Box 260, CH-9471 Buchs, Switzerland Biological Assay The *Haemonchus contortus* L3 (HcL3) test is used to measure the biological activities of the compounds claimed. The assay involves in vitro testing against *H. contortus* conducted according to the following general procedure.

HcL3 larvae were collected from infected sheep and, after cleaning, stored in water at 12° C. for up to one month. Viable infective larvae were exsheathed using 10% hypochlorite in Glucose Tyrodes balanced salt solution containing antibiotics and resuspended in basal medium (20 g/l bacto-tryptone, 5 g/l yeast extract, 57 g/l glucose, 0.8 g/l di-Potassium hydrogen orthophosphate, 0.8 g/l potassium dihydrogen orthophosphate and 2 µM Hepes with antibiotics). 95 µl worm suspension was added to each well of a 96 well plate.

Test compounds were dissolved in dimethylsulfoxide to give a working stock solution of 20 mg/ml. The stock concentration was diluted 1:10 in Basal media to give 2.0 mg/ml (10% DMSO). 5 µl of the stock compound solution was added to the worm suspension to give a final concentration of 100 µg/ml. Plates were sealed with pressure sensitive film and incubated at 37° C. Observations were made 2 hrs, 24 hrs, 48 hrs, 72 hrs and 4 days post-treatment using an inverted microscope. Activity was recorded if a significant proportion of the worms were dead or adversely affected by the compound when compared to the control well containing 1% DMSO. Compounds were initially tested at 100 µg/ml, wherefrom relevant dose responses (100, 30, 10, 3, 1, 0.3, 0.1 µg/ml) were conducted in duplicate experiments to generate n=2. Data was recorded as minimum effective dose.

Example 1

N-[1-Cyano-1-(5-cyano-2,3-dihydro-1-benzofuran-2-yl)ethyl]-4-(trifluoromethoxy)benzamide

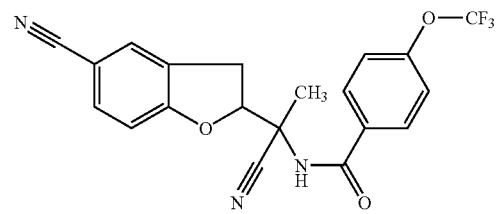

To a solution of the compound of Preparation 1 (14.4 g, 67.5 mmol) and N,N-diisopropylethylamine (14.0 ml, 81.0 mmol) in tetrahydrofuran (100 ml), at 0° C., was added dropwise 4-(trifluoromethoxy)benzoyl chloride (10.8 ml, 70.9 mmol) in tetrahydrofuran (5 ml). The reaction mixture was stirred at room temperature for 18 h and then concentrated in vacuo. To the residue was added ethyl acetate (200 ml) and the solution was washed with hydrochloric acid (0.1M, 80 ml), saturated aqueous sodium hydrogen carbonate solution (100 ml) and brine (50 ml), dried (MgSO₄) and concentrated in vacuo. A portion of the residue (approximately 5 g) was purified by column chromatography (silica), eluting with 1% methanol in dichloromethane. The appropriate fractions were combined and concentrated give the compound of Example 1a (1.4 g) as a mixture of 4 diastereoisomers.

The compound of Example 1a (approximately 3 g) was purified by automated flash chromatography (Biotage™, 65M silica cartridge) with gradient elution, ethyl acetate cyclohexane [5:95 to 60:40]. The appropriate fractions were combined and concentrated to give the compound of Example 1b (1.3 g) as a pair of enantiomers.

The compound of Example 1b (200 mg, 0.5 mmol) was dissolved in ethanol (4 ml) and the enantiomers were separated by automated preparative liquid chromatography (Gilson system, 250×50 mm ID Chiralcel AD, 20 µm column, 50 ml/min) using ethanol hexane [20:80] as the mobile phase. The appropriate fractions were combined and concentrated to give two enantiomerically pure products, the compound of Example 1c (66 mg) and the compound of Example 1d (65 mg).

| Example | Structure Comment | Retention Time (min) | MH+ Found/ Expected | H.c. (L3) MED µg/ml |
|---|---|---|---|---|
| 1a | Mixture of 4 diastereoisomers | — | 402.0 / 402.1 | 3 |
| 1b | Second eluting pair of enantiomers | — | 402.1 / 402.1 | |
| 1c | Single enantiomer | 15.36 | 402.2 / 402.1 | |
| 1d | Single enantiomer | 33.87 | 402.2 / 402.1 | |

Example 1a

¹H-NMR (CDCl₃): 1.76-1.78 and 1.90-1.92 (3H), 3.39-3.46 (1H), 3.46-3.60 (1H), 5.20-5.24 and 5.59-5.62 (1H), 6.37-6.39 and 6.52-6.54 (1H), 6.86-6.91 (1H), 7.30-7.34 (2H), 7.48-7.51 (2H), 7.80-7.85 (2H)

Example 1b

¹H-NMR (CDCl₃): 1.72-1.75 (3H), 3.35-3.40 (1H), 3.46-3.51 (1H), 5.58-5.61 (1H), 6.32-6.35 (1H), 6.90-6.92 (1H), 7.30-7.33 (2H), 7.49-7.51 (2H), 7.81-7.83 (2H)

Example 1c

Retention time=15.36 min 250×4.6 mm Chiralcel AD-H, 5 µm column, ethanol:hexane [20:80], 1 ml/min
¹H-NMR (CDCl₃): 1.89-1.92 (3H), 3.40-3.45 (1H), 3.52-3.58 (1H), 5.21-5.25 (1H), 6.90-6.93 (1H), 7.28-7.31 (2H), 7.50-7.53 (2H), 7.79-7.83 (2H)

Example 1d

Retention time=33.87 min 250×4.6 mm Chiralcel AD-H, 5 µm column, ethanol:hexane [20:80], 1 ml/min
¹H-NMR (CDCl₃): 1.88-1.92 (3H), 3.40-3.46 (1H), 3.52-3.59 (1H), 5.21-5.26 (1H), 6.92-6.95 (1H), 7.29-7.33 (2H), 7.49-7.53 (2H), 7.80-7.84 (2H)

Example 2

N-[1-Cyano-1-(5-cyano-2,3-dihydro-1-benzofuran-2-yl)ethyl]-4-[(trifluoromethyl)thio]benzamide

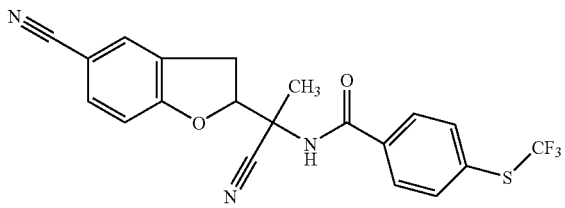

To a solution of the compound of Preparation 1 (216 mg, 1.0 mmol) and N,N-diisopropylethylamine (0.2 ml, 1.2 mmol) in tetrahydrofuran (3 ml), at 0° C., was added dropwise 4-(trifluoromethylthio)benzoyl chloride (302 mg, 1.2 mmol) in tetrahydrofuran (1 ml). The reaction mixture was allowed to warm to room temperature over 2 h and then concentrated in vacuo. The residue was washed with water and brine and extracted with ethyl acetate. The combined extracts were dried (MgSO₄) and concentrated in vacuo. The residue was dissolved in acetonitrile (2 ml) with a few drops of dimethyl sulphoxide and purified by automated preparative liquid chromatography (Gilson system, 150 mm×50 mm LUNA C18(2) 10 µm column, 120 ml/min) using an acetonitrile:water gradient [55:45 (for 16 min) to 98:2 (for 3 min) to 55:45 (for 1 min)]. The appropriate fractions were concentrated in vacuo to give the title compound (116 mg) as a mixture of 4 diastereoisomers.

Experimental (M-H⁺)⁻ 416.1; expected 416.1

¹H-NMR (CDCl₃): 1.75-1.77 and 1.88-1.90 (3H), 3.37-3.43 (1H), 3.50-3.60 (1H), 5.27-5.31 and 5.57-5.61 (1H), 6.77-6.83 (1H), 6.89-6.95 (1H), 7.50-7.54 (1H), 7.75-7.79 (2H), 7.80-7.88 (2H) in vitro H.c. (L3) MED=3 µg/ml Example 3

N-[1-Cyano-1-(2,3-dihydro-1-benzofuran-2-yl)ethyl]-4-(trifluoromethoxy)benzamide

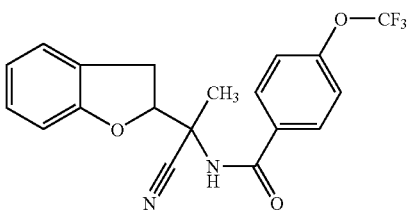

To a solution of the compound of Preparation 2 (144 mg, 0.7 mmol) and N,N-diisopropylethylamine (0.1 ml, 0.8 mmol) in tetrahydrofuran (5 ml), at 0° C., was added dropwise 4-(trifluoromethoxy)benzoyl chloride (190 mg, 0.8 mmol) in tetrahydrofuran (1 ml). The reaction mixture was allowed to warm to room temperature over 2 h and then concentrated in vacuo. The residue was washed with water and brine and extracted with ethyl acetate. The combined extracts were dried (MgSO₄) and concentrated in vacuo. The residue was dissolved in acetonitrile (2 ml) and purified by automated preparative liquid chromatography (Gilson system, 150 mm×50 mm LUNA C18(2) 10 µm column, 120 ml/min) using an acetonitrile:water gradient [55:45 (for 20 min) to 98:2 (for 3 min) to 55:45 (for 1 min)]. The appropriate fractions were concentrated in vacuo to give the title compound (91 mg) as a mixture of 4 diastereoisomers. Experimental MH⁺ 377.1; expected 377.1

¹H-NMR (CDCl₃): 1.74-1.76 and 1.92-1.94 (3H), 3.30-3.60 (2H), 5.00-5.03 and 5.37-5.40 (1H), 6.47-6.50 and 6.60-6.63 (1H), 6.80-6.84 (1H), 6.95-6.99 (1H), 7.17-7.20 (1H), 7.21-7.28 (3H), 7.72-7.75 (1H), 7.80-7.83 (1H) in vitro H.c. (L3) MED=30 µg/ml

Example 4

N-[1-(5-Bromo-2,3-dihydro-1-benzofuran-2-yl)-1-cyanoethyl]-4-(trifluoromethyl)benzamide

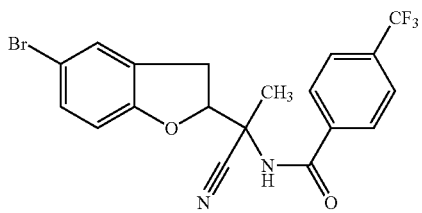

To a solution of the compound of Preparation 3 (241 mg, 0.9 mmol) and N,N-diisopropylethylamine (0.2 ml, 1.1 mmol) in tetrahydrofuran (5 ml), at 0° C., was added dropwise 4-(trifluoromethyl)benzoyl chloride (233 mg, 1.1 mmol) in tetrahydrofuran (1 ml). The reaction mixture was allowed to warm to room temperature over 2 h and then concentrated in vacuo. The residue was washed with water and brine and extracted with ethyl acetate. The combined extracts were dried (MgSO$_4$) and concentrated in vacuo. The residue was dissolved in acetonitrile (1.8 ml) with a few drops of dimethyl sulphoxide and purified by automated preparative liquid chromatography (Gilson system, 150 mm×50 mm LUNA C18(2) 10 μm column, 120 ml/min) using an acetonitrile:water gradient [60:40 (for 18 min) to 98:2 (for 3 min) to 60:40 (for 1 min)]. The appropriate fractions were concentrated in vacuo to give the title compound (223 mg) as a mixture of 4 diastereoisomers.

Experimental MH$^+$ 439.8; expected 439.0

$^1$H-NMR (CDCl$_3$): 1.72-1.73 and 1.95-1.96 (3H), 3.40-3.60 (2H), 5.02-5.07 and 5.40-5.45 (1H), 6.42-6.44 and 6.60-6.62 (1H), 7.37-7.38 and 7.53-7.54 (1H), 7.70-7.79 (3H), 7.80-7.90 (2H), 8.18-8.20 and 8.25-8.27 (1H)

Example 5

N-[1-(5-Chloro-2,3-dihydro-1-benzofuran-2-yl)-1-cyanoethyl]-4-(trifluoromethyl)benzamide

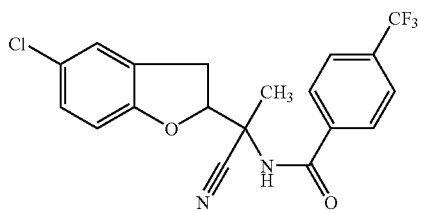

To a solution of the compound of Preparation 4 (266 mg, 1.2 mmol) and N,N-diisopropylethylamine (0.3 ml, 1.4 mmol) in tetrahydrofuran (5 ml), at 0° C., was added dropwise 4-(trifluoromethyl)benzoyl chloride (308 mg, 1.4 mmol) in tetrahydrofuran (1 ml). The reaction mixture was allowed to warm to room temperature over 2 h and then concentrated in vacuo. The residue was washed with water and brine and extracted with ethyl acetate. The combined extracts were dried (MgSO$_4$) and concentrated in vacuo. The residue was dissolved in acetonitrile (2 ml) with a few drops of dimethyl sulphoxide and purified by automated preparative liquid chromatography (Gilson system, 150 mm×50 mm LUNA C18(2) 10 μm column, 120 ml/min) using an acetonitrile:water gradient [60:40 (for 18 min) to 98:2 (for 3 min) to 60:40 (for 1 min)]. The appropriate fractions were concentrated in vacuo to give the title compound (161 mg) as a mixture of 4 diastereoisomers.

Experimental MH$^+$ 393.8; expected 394.1

$^1$H-NMR (CDCl$_3$): 1.73-1.75 and 1.92-1.93 (3H), 3.30-3.60 (2H), 5.04-5.08 and 5.40-5.43 (1H), 6.42-6.44 and 6.60-6.62 (1H), 7.10-7.18 (1H), 7.71-7.79 (3H), 7.80-7.90 (2H), 8.18-8.20 and 8.25-8.27 (1H) in vitro H.c. (L3) MED=30 μg/ml

Example 6

N-[1-Cyano-1-(7-cyano-2,3-dihydro-1-benzofuran-2-yl)ethyl]-4-(trifluoromethoxy)benzamide

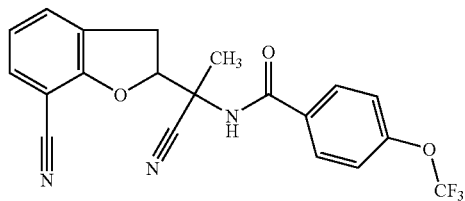

To a solution of the compound of Preparation 5 (139 mg, 0.7 mmol) and N,N-diisopropylethylamine (0.1 ml, 0.8 mmol) in tetrahydrofuran (2 ml), at 0° C. and under nitrogen, was added dropwise 4-(trifluoromethoxy)benzoyl chloride (176 mg, 0.8 mmol) in tetrahydrofuran (0.2 ml). The reaction mixture was allowed to warm to room temperature and stirred for 18 h before addition of water (5 ml) and ethyl acetate (5 ml). The two layers were separated and the aqueous layer was extracted with ethyl acetate (2×7 ml). The combined organic phases were washed with aqueous potassium carbonate solution (10%), saturated aqueous ammonium chloride solution and brine, dried (MgSO$_4$) and concentrated in vacuo. The residue was dissolved in acetonitrile (2 ml) and purified by automated preparative liquid chromatography (Gilson system, 150 mm×50 mm LUNA C18(2) 10 μm column, 120 ml/min) using an acetonitrile:water gradient [55:45 (for 15 min) to 98:2 (for 3 min) to 55:45 (for 1 min)]. The appropriate fractions were concentrated in vacuo to give the title compound (109 mg) as a mixture of 4 diastereoisomers.

Experimental (M-H$^+$)$^-$ 400.1; expected 400.1

$^1$H-NMR (CDCl$_3$): 1.96-1.97 and 1.98-2.00 (3H), 3.39-3.43 and 3.51-3.61 (2H), 5.20-5.23 and 5.62-5.65 (1H), 7.00-7.03 (1H), 7.29-7.35 (2H), 7.39-7.45 (2H), 7.80-7.82 and 7.83-7.85 (2H) in vitro H.c. (L3) MED=10 μg/ml Similarly prepared to Example 6 from the compound of Preparation 5 and 4-(trifluoromethylthio)benzoyl chloride was:

Example 7

N-[1-Cyano-1-(7-cyano-2,3-dihydro-1-benzofuran-2-yl)ethyl]-4-[(trifluoromethyl)thio]benzamide

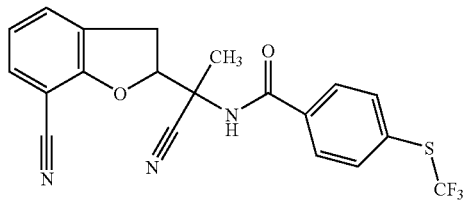

Experimental (M-H+)⁻ 416.1; expected 416.1

¹H-NMR (CDCl₃): 1.96-1.97 and 1.98-2.00 (3H), 3.39-3.44 and 3.54-3.65 (2H), 5.20-5.23 and 5.63-5.65 (1H), 7.00-7.03 (1H), 7.39-7.45 (2H), 7.74-7.80 (3H), 7.83-7.85 (1H) in vitro H.c. (L3) MED=10 µg/ml

Example 8

N-[1-(7-Chloro-5-cyano-2,3-dihydro-1-benzofuran-2-yl)-1-cyanoethyl]-4-(trifluoromethoxy)benzamide

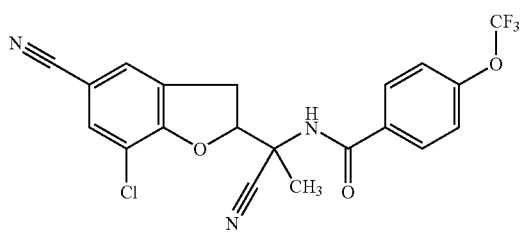

To a solution of the compound of Preparation 19 (164 mg, 0.6 mmol) and N,N-diisopropylethylamine (0.13 ml, 0.8 mmol) in dichloromethane (1 ml), at 0° C., was added dropwise 4-(trifluoromethoxy)benzoyl chloride (144 mg, 0.7 mmol) in dichloromethane (1 ml). The reaction mixture was allowed to warm to room temperature and stirred for 2 h, before addition of water (10 ml). The organic phase was separated and passed through a hydrophobic filter (Whatman 1PS) and the filtrate was concentrated under a stream of nitrogen. The residue was dissolved in acetonitrile (1.5 ml) and purified by automated preparative liquid chromatography (Gilson system, 150 mm×50 mm LUNA C18(2) 10 µm column, 120 ml/min) using an acetonitrile:water gradient [55:45 (for 17 min) to 98:2 (for 3 min) to 55:45 (for 1 min)]. The appropriate fractions were combined and concentrated to give the title compound (61 mg) as a mixture of 4 diastereoisomers.

Experimental MH⁺ 436.0; expected 436.1

¹H-NMR (d₆-Acetone): 1.79-1.81 and 1.83-1.86 (3H), 3.60-3.70 and 3.80-3.85 (2H), 5.75-5.79 and 5.86-5.90 (1H), 7.41-7.45 (2H), 7.60-7.70 (2H), 8.01-8.05 (2H) in vitro H.c. (L3) MED <1 µg/ml

Example 9

N-[1-(7-Chloro-5-cyano-2,3-dihydro-1-benzofuran-2-yl)-1-cyanoethyl]-4-(pentafluorothio)benzamide

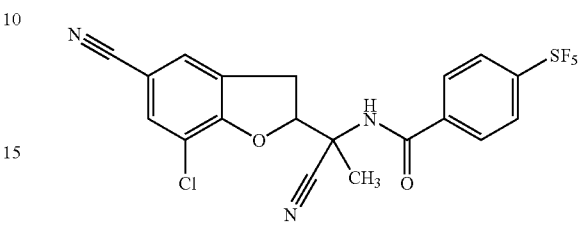

To a solution of the compound of Preparation 19 (154 mg, 0.5 mmol) and N,N-diisopropylethylamine (0.10 ml, 0.6 mmol) in dichloromethane (1 ml), at 0° C., was added dropwise the compound of Preparation 24 (137 mg, 0.5 mmol) in dichloromethane (1 ml). The reaction mixture was allowed to warm to room temperature and stirred for 2 h, before addition of water (10 ml). The organic phase was separated and passed through a hydrophobic filter (Whatman 1PS) and the filtrate was concentrated under a stream of nitrogen. The residue was dissolved in acetonitrile (3 ml) and purified by automated preparative liquid chromatography (Gilson system, 150 mm×50 mm LUNA C18(2) 10 µm column, 120 ml/min) using an acetonitrile:water gradient [55:45 (for 19 min) to 98:2 (for 3 min) to 55:45 (for 1 min)]. The appropriate fractions were combined and concentrated to give the title compound (153 mg) as a mixture of 4 diastereoisomers.

Experimental MH⁺ 478.0; expected 478.0

¹H-NMR (d₆-Acetone): 1.80-1.82 and 1.83-1.85 (3H), 3.60-3.75 and 3.80-3.85 (2H), 5.76-5.79 and 5.84-5.87 (1H), 7.60-7.65 (1H), 7.70-7.73 (1H), 8.00-8.03 (2H), 8.09-8.12 (2H) in vitro H.c. (L3) MED <1 µg/ml

PREPARATIONS

The following Preparations illustrate the synthesis of certain intermediates used in the preparation of the preceding Examples.

Preparation 1

2-(1-Amino-1-cyanoethyl)-2,3-dihydro-1-benzofuran-5-carbonitrile

A mixture of the compound of Preparation 6 (203 mg, 1.1 mmol), ammonium chloride (90 mg, 1.7 mmol) and ammonia (7N solution in methanol, 3.1 ml, 21.7 mmol) was stirred at room temperature for 10 min, before addition of sodium cyanide (69 mg, 1.4 mmol). The reaction mixture was stirred for 2 h and then concentrated in vacuo. To the residue was added ethyl acetate and the solution was filtered. The filtrate was concentrated in vacuo to give the title compound (216 mg).

Experimental MH$^+$ 214.3; expected 214.1

Similarly prepared were:

| Prep. no. | Name | MH$^+$ Found/ Expected | From Prep. |
|---|---|---|---|
| 2 | 2-Amino-2-(2,3-dihydro-1-benzofuran-2-yl)propanenitrile | 189.7 189.1 | 11 |
| 3 | 2-Amino-2-(5-bromo-2,3-dihydro-1-benzofuran-2-yl)propanenitrile | 269.6 267.0 | 13 |
| 4 | 2-Amino-2-(5-chloro-2,3-dihydro-1-benzofuran-2-yl)propanenitrile | 223.6 223.1 | 14 |
| 5 | 2-(1-Amino-1-cyanoethyl)-2,3-dihydro-1-benzofuran-7-carbonitrile | | 15 |

Preparation 5

2-(1-Amino-1-cyanoethyl)-2,3-dihydro-1-benzofuran-7-carbonitrile $^1$H-NMR (CD$_3$OD): 1.43-1.44 and 1.60-1.61 (3H), 3.40-3.44 (2H), 4.89-4.92 (1H), 6.99-7.02 (1H), 7.37-7.40 (1H), 7.78-7.50 (1H)

Preparation 6

2-Acetyl-2,3-dihydro-1-benzofuran-5-carbonitrile

A mixture of the compound of Preparation 7 (413 mg, 1.4 mmol), tetrabutylammonium bromide (463 mg, 1.4 mmol) and copper cyanide (257 mg, 2.9 mmol) in water (1 ml) was heated at 170° C. in a microwave oven (100W) for 3 min. To the mixture was added water (2 ml) and the two layers were separated. The aqueous layer was extracted with diethyl ether and to the organic phase was added acetonitrile. The organic phase was filtered and the filtrate was combined with the organic extracts, dried (MgSO$_4$) and concentrated in vacuo. The residue was purified by column chromatography (silica), eluting with dichloromethane. The appropriate fractions were combined and concentrated to give the title compound (208 mg).

Experimental MH$^+$ 188.1; expected 188.1

Preparation 7

1-(5-Iodo-2,3-dihydro-1-benzofuran-2-yl)ethanone

To a solution of the compound of Preparation 8 (39.8 g, 119.0 mmol) in tetrahydrofuran (300 ml), at 0° C. and under nitrogen, was added dropwise methylmagnesium chloride (3M in diethyl ether, 83.8 ml, 239.0 mmol). The reaction mixture was stirred at 0° C. for 1 h and then quenched by addition of aqueous ammonium chloride solution (10%, 35 ml). The mixture was concentrated in vacuo and to the residue was added aqueous ammonium chloride solution (10%, 200 ml). The mixture was extracted with ethyl acetate (3×100 ml) and the combined extracts were, dried (MgSO$_4$) and concentrated in vacuo to give the title compound (28.4 g).

$^1$H-NMR (CDCl$_3$): 2.26-2.28 (3H), 3.22-3.25 (1H), 3.41-3.44 (1H), 5.00-5.03 (1H), 6.60-6.62 (1H), 7.40-7.43 (2H)

Preparation 8

5-Iodo-N-methoxy-N-methyl-2,3-dihydro-1-benzofuran-2-carboxamide

To a solution of the compound of Preparation 9 (2.4 g, 8.4 mmol) in anhydrous dichloromethane (20 ml), under nitrogen, was added 1,1'-carbonyldiimidazole (1.5 g, 9.3 mmol). After stirring for 3 days, N,O-dimethylhydroxylamine hydrochloride (903 mg, 9.3 mmol) was added and the reaction mixture was stirred at room temperature for 18 h. The mixture was washed with hydrochloric acid (1N), followed by 10% aqueous potassium carbonate solution, and the organic phase was separated, dried (MgSO$_4$) and concentrated in vacuo to give the title compound (1.6 g).

$^1$H-NMR (CDCl$_3$): 3.16-3.21 (3H), 3.32-3.40 (2H), 3.69-3.72 (3H), 5.41-5.48 (1H), 6.55-6.59 (1H), 7.31-7.39 (2H)

Preparation 9

5-Iodo-2,3-dihydro-1-benzofuran-2-carboxylic acid

To a solution of the compound of Preparation 10 (39.5 g, 241.0 mmol) in acetic acid (395 ml) was added benzyltrimethylammonium dichloroiodate (125.0 g, 359.0 mmol) and zinc chloride (49.5 g, 363.0 mmol). The reaction mixture was stirred at room temperature for 40 h and then quenched with water (500 ml) and tert-butyl methyl ether (200 ml). The mixture was extracted with dichloromethane (6×200 ml) and the combined extracts were washed with aqueous sodium thiosulphate solution (10%, 3×250 ml) and brine (200 ml), dried (MgSO$_4$) and concentrated in vacuo. To the residue was added cyclohexane (200 ml) and the solution was heated to reflux, before addition of tert-butyl methyl ether to solubilize the residue. The solution was cooled to 0° C. and the resulting precipitate was collected by filtration and dried in vacuo to give the title compound (44.1 g).

Experimental (M-H$^+$)$^-$ 289.0; expected 289.0

Preparation 10

2,3-Dihydro-1-benzofuran-2-carboxylic acid

A mixture of 1-benzofuran-2-carboxylic acid (40.0 g, 250.0 mmol) and palladium hydroxide (20 wt. % on carbon, 2.0 g) in acetic acid (400 ml) was heated at 60° C. under a hydrogen atmosphere (80 psi) for 2 h. The mixture was filtered to give a solution of the title compound (39.5 g) in acetic acid.

$^1$H-NMR (d$_6$-DMSO): 3.19-3.23 (1H), 3.50-3.54 (1H), 5.16-5.20 (1H), 6.78-6.82 (2H), 7.09-7.12 (1H), 7.18-7.20 (1H)

Preparation 11

1-(2,3-Dihydro-1-benzofuran-2-yl)ethanone

To a solution of Preparation 12 (352 mg, 1.7 mmol) in tetrahydrofuran (10 ml), at 0° C. and under nitrogen, was added dropwise methylmagnesium bromide (3M in diethyl ether, 1.13 ml, 3.4 mmol). The reaction mixture was stirred at 0° C. for 1 h and then quenched by addition of saturated aqueous ammonium chloride solution. The mixture was extracted with ethyl acetate (3×50 ml) and the combined extracts were washed with brine, dried (MgSO$_4$) and concentrated in vacuo to give the title compound (246 mg).

Experimental MH$^+$ 163.2; expected 163.1

Preparation 12

N-Methoxy-N-methyl-2,3-dihydro-1-benzofuran-2-carboxamide

To a solution of 2,3-dihydro-1-benzofuran-2-carboxylic acid (500 mg, 3.1 mmol) in anhydrous dichloromethane (20 ml), under nitrogen, was added 1,1'-carbonyldiimidazole (543 mg, 3.4 mmol). After stirring for 1 h, N,O-dimethylhydroxylamine hydrochloride (327 mg, 3.4 mmol) was added and the reaction mixture was stirred at room temperature for 18 h. The mixture was washed with hydrochloric acid (1N), followed by 10% aqueous potassium carbonate solution, and the organic phase was separated, dried ($MgSO_4$) and concentrated in vacuo to give the title compound (352 mg).

Experimental $MH^+$ 208.2; expected 208.1

Preparation 13

1-(5-Bromo-2,3-dihydro-1-benzofuran-2-yl)ethanone

A mixture of the compound of Preparation 7 (288 mg, 1.0 mmol) and anhydrous nickel (II) bromide (437 mg, 2.0 mmol) in N,N-dimethylformamide (0.5 ml) was sonicated for 20 min and then heated at 170° C. in a microwave oven (100W) for 5 min. The mixture was partitioned between water (20 ml) and diethyl ether (20 ml) and the two layers were separated. The aqueous layer was re-extracted with diethyl ether and the combined organic phases were dried ($MgSO_4$) and concentrated in vacuo to give the title compound (228 mg).

$^1$H-NMR ($CDCl_3$): 2.24-2.26 (3H), 3.22-3.26 (1H), 3.40-3.45 (1H), 5.00-5.03 (1H), 6.74-6.77 (1H), 7.20-7.25 (2H)

Preparation 14

1-(5-Chloro-2,3-dihydro-1-benzofuran-2-yl)ethanone

A mixture of the compound of Preparation 7 (288 mg, 1.0 mmol) and anhydrous nickel (II) chloride (475 mg, 2.0 mmol) in N,N-dimethylformamide (0.5 ml) was sonicated for 20 min and then heated at 170° C. in a microwave oven (100 W) for 5 min. The mixture was partitioned between water (20 ml) and diethyl ether (20 ml) and the two layers were separated. The aqueous layer was extracted with diethyl ether and the combined organic phases were dried ($MgSO_4$) and concentrated in vacuo to give the title compound (243 mg).

$^1$H-NMR ($CDCl_3$): 2.25-2.27 (3H), 3.22-3.27 (1H), 3.40-3.46 (1H), 5.00-5.04 (1H), 6.80-6.83 (1H), 7.10-7.20 (2H)

Preparation 15

2-Acetyl-2,3-dihydro-1-benzofuran-7-carbonitrile

To a solution of Preparation 16 (457 mg, 2.4 mmol) in dichloromethane (12 ml) was added Dess-Martin periodinane (1.1 g, 2.7 mmol) in dichloromethane (18 ml). The reaction mixture was stirred at room temperature for 60 h and then poured into diethyl ether (30 ml). The mixture was washed with aqueous sodium hydroxide solution (1N) and the organic phase was separated, washed with brine, dried ($MgSO_4$) and concentrated in vacuo to give the title compound (340 mg).

$^1$H-NMR ($CDCl_3$): 2.38-2.40 (3H), 3.40-3.50 (2H), 5.17-5.20 (1H), 6.96-6.99 (1H), 7.39-7.41 (2H)

Preparation 16

2-(1-Hydroxyethyl)-2,3-dihydro-1-benzofuran-7-carbonitrile

To a solution of Preparation 17 (487 mg, 2.8 mmol) in dichloromethane (10 ml), at 0° C. and under nitrogen, was added 3-chloroperoxybenzoic acid (606 mg, 3.5 mmol). The reaction mixture was allowed to warm to room temperature and stirred for 18 h. The mixture was washed with aqueous potassium carbonate solution and the organic phase was separated, washed with brine, dried ($MgSO_4$) and concentrated in vacuo to give the title compound (457 mg), which was used directly in the next stage.

Preparation 17

3-[(2E)-But-2-en-1-yl]-2-hydroxybenzonitrile

A mixture of Preparation 18 (900 mg, 5.2 mmol) and N,N-diethylaniline (1 ml) was heated in a microwave oven (300 W) at 250° C. for 30 min. The reaction mixture was partitioned between diethyl ether and hydrochloric acid (1N) and the two layers were separated. The organic phase was washed with brine, dried ($MgSO_4$) and concentrated in vacuo to give the title compound (487 mg).

$^1$H-NMR ($CDCl_3$): 1.74-1.76 (3H), 3.38-3.40 (2H), 5.55-5.65 (2H), 7.02-7.04 (1H), 7.16-7.20 (2H)

Preparation 18

2-[(1-Methylprop-2-en-1-yl)oxy]benzonitrile

To a mixture of salicylonitrile (2.0 g, 16.8 mmol) and but-3-en-2-ol (1.5 ml, 16.8 mmol) in tetrahydrofuran (100 ml) was added triphenylphosphine (4.4 g, 16.8 mmol), followed by diisopropyl azodicarboxylate (3.3 ml, 16.8 mmol) in tetrahydrofuran (15 ml), added dropwise ensuring the reaction temperature did not rise above 20° C. The reaction mixture was stirred at room temperature for 18 h and then concentrated in vacuo. To the residue was added diethyl ether (20 ml) and the solution was washed with aqueous sodium hydroxide solution (1N), dried ($MgSO_4$) and concentrated in vacuo. The residue was purified by flash chromatography (silica) with gradient elution, diethyl ether:cyclohexane [1:9 to 1:1]. The appropriate fractions were combined and concentrated to give the title compound (1.9 g).

$^1$H-NMR ($CDCl_3$): 1.45-1.46 (3H), 4.81-4.84 (1H), 5.18-5.20 (1H), 5.24-5.26 (1H), 5.82-5.86 (1H), 6.97-7.00 (2H), 7.40-7.42 (1H), 7.48-7.50 (1H)

Preparation 19

2-(1-Amino-1-cyanoethyl)-7-chloro-2,3-dihydro-1-benzofuran-5-carbonitrile

A mixture of the compound of Preparation 20 (189 mg, 0.9 mmol), ammonium chloride (71 mg, 1.3 mmol) and ammonia (2M solution in methanol, 8.5 ml, 17.1 mmol) was stirred at room temperature for 20 min, before addition of sodium cyanide (55 mg, 1.1 mmol). The reaction mixture was stirred for 19 h and additional ammonium chloride (71 mg, 1.3 mmol), ammonia (2M solution in methanol, 8.5 ml, 17.1 mmol) and sodium cyanide (55 mg, 1.1 mmol) was added. The reaction mixture was stirred at room temperature for 80 h and then quenched by addition of aqueous sodium hydroxide solution (2M, 30 ml). The mixture was extracted with toluene (3×100 ml) and the combined extracts were washed with brine, dried (MgSO$_4$) and concentrated in vacuo to give the title compound (154 mg).

$^1$H-NMR (CDCl$_3$): 1.55-1.60 (3H), 3.40-3.48 (2H), 4.79-4.81 and 4.84-4.86 (1H), 7.38-7.40 (1H), 7.47-7.49 (1H)

Preparation 20

2-Acetyl-7-chloro-2,3-dihydro-1-benzofuran-5-carbonitrile

To a solution of the compound of Preparation 21 (615 mg, 1.9 mmol) in tert-butyl methyl ether (55 ml) was added Dess-Martin periodinane (980 mg, 2.3 mmol) and the reaction mixture was stirred at room temperature for 22 h. To the mixture was added tert-butyl methyl ether (30 ml) and the solution was washed with aqueous sodium hydroxide solution (1M, 4×100 ml) and brine, dried (MgSO$_4$) and concentrated in vacuo. The residue was dissolved in acetonitrile (3 ml) with a few drops of dimethyl sulphoxide and purified by automated preparative liquid chromatography (Gilson system, 150 mm×50 mm LUNA C18(2) 10 μm column, 120 ml/min) using an acetonitrile:water gradient [40:60 (for 15 min) to 98:2 (for 3 min) to 40:60 (for 1 min)]. The appropriate fractions were combined and concentrated to give the title compound (155 mg).

$^1$H-NMR (CDCl$_3$): 2.10-2.12 (3H), 3.20-3.22 (1H), 3.58-3.60 (1H), 6.99-7.00 (1H), 7.40-7.41 (1H), 7.52-7.53 (1H)

Preparation 21

7-Chloro-2-(1-hydroxyethyl)-2,3-dihydro-1-benzofuran-5-carbonitrile

To a solution of the compound of Preparation 22 (1.3 g, 5.5 mmol) in dichloromethane (45 ml), at 0° C. and under nitrogen, was added 3-chloroperoxybenzoic acid (50% purity, 3.3 g, 9.6 mmol). The reaction mixture was allowed to warm to room temperature and stirred for 18 h. The mixture was washed with aqueous potassium carbonate solution (5%, 3×75 ml) and the organic phase was separated, washed with brine, dried (MgSO$_4$) and concentrated in vacuo to give the title compound (591 mg).

$^1$H-NMR (CDCl$_3$): 1.21-1.23 (3H), 3.20-3.23 (1H), 3.37-3.40 (1H), 4.21-4.23 (1H), 4.84-4.86 (1H), 7.35-7.36 (1H), 7.42-7.43 (1H)

Preparation 22

3-[(2)-But-2-en-1-yl]-5-chloro-4-hydroxybenzonitrile

A mixture of the compound of Preparation 23 (1.4 g, 6.3 mmol) and N,N-diethylaniline (1.54 ml) was heated in a CEM Discover™ microwave oven (300 W) at 200° C. for 10 min. To the reaction mixture was added tert-butyl methyl ether (50 ml) and the solution was washed with hydrochloric acid (1M, 3×50 ml). The organic phase was washed with aqueous sodium hydroxide solution (1M, 3×50 ml) and the combined base washes were adjusted to pH 1 by addition of concentrated hydrochloric acid and extracted with tert-butyl methyl ether (3×100 ml). The combined organic phases were dried (MgSO$_4$) and concentrated in vacuo to give the title compound (1.1 g). Experimental MH$^+$ 208.2; expected 208.1

Preparation 23

3-Chloro-4-[(1-methylprop-2-en-1-yl)oxy]benzonitrile

To a mixture of polymer-supported triphenylphosphine (470 mg, 19.0 mmol) and 3-chloro-4-hydroxybenzonitrile (2.0 g, 13.0 mmol) in anhydrous tetrahydrofuran (28 ml) was added a solution of diisopropyl azodicarboxylate (2.8 g, 13.8 mmol) in anhydrous tetrahydrofuran (27 ml). After stirring for 30 min, but-3-en-2-ol (1.1 ml, 13.0 mmol) in anhydrous tetrahydrofuran (43 ml) was added and the reaction mixture was stirred at room temperature for 4 h. The mixture was filtered, washing through with anhydrous tetrahydrofuran (2×40 ml), and the filtrate was concentrated in vacuo. To the residue was added tert-butyl methyl ether (40 ml) and the solution was washed with aqueous sodium hydroxide (1M, 3×100 ml) and brine, dried (MgSO$_4$) and concentrated in vacuo. The residue was triturated with cyclohexane (30 ml) to give the title compound (1.7 g).

$^1$H-NMR (CDCl$_3$): 1.52-1.54 (3H), 4.85-4.88 (1H), 5.21-5.29 (2H), 5.84-5.90 (1H), 6.98-7.00 (1H), 7.42-7.44 (1H), 7.61-7.62 (1H)

Preparation 24

4-(Pentafluorothio)benzoyl chloride

A solution of the compound of Preparation 25 (8.5 g, 34.3 mmol) in thionyl chloride (50 ml) was heated at 65° C. for 4 h. The mixture was concentrated in vacuo and the residue was triturated with toluene to give the title compound (7.6 g).

$^1$H-NMR (CDCl$_3$): 7.95-8.00 (2H), 8.21-8.26 (2H)

Preparation 25

4-(Pentafluorothio)benzoic acid

A mixture of the compound of Preparation 26 (8.0 g, 34.8 mmol) and sodium periodate (30.5 g, 142.0 mmol) in acetonitrile (60 ml), carbon tetrachloride (60 ml) and water (60 ml) was de-gassed and treated with ruthenium (III) chloride hydrate (157 mg, 0.7 mmol). The reaction mixture was stirred at room temperature for 1 h and then partitioned between diethyl ether and water. The two layers were separated and the organic phase was washed with aqueous sodium hydroxide solution (1N). The aqueous phase was adjusted to pH 1 by addition of hydrochloric acid and then extracted with diethyl ether. The combined extracts were washed with brine, dried (MgSO$_4$) and concentrated in vacuo to give the title compound (2.8 g).

Experimental (M-H$^+$)$^-$ 247.1; expected 247.0

Preparation 26

1-(Pentafluorothio)-4-vinylbenzene

A mixture of the compound of Preparation 27 (16.6 g, 50.4 mmol), tributyl(vinyl)tin (22.1 ml, 24.0 g, 75.6 mmol) and tetrakis(triphenylphosphine)palladium(0) (2.1 g, 1.8 mmol) in N,N-dimethylformamide (170 ml) was purged with nitrogen and heated at 100° C. for 1.5 h. The mixture was partitioned between diethyl ether and water and the organic phase was separated, washed with aqueous potassium fluoride solution (2×50 ml) and brine, dried (MgSO$_4$) and concentrated in vacuo. The residue was purified by column chromatography (silica, 800 g), eluting with pentane. The residue was further purified by distillation to give the title compound (18.0 g).

$^1$H-NMR (CDCl$_3$): 5.39-5.43 (1H), 5.80-5.84 (1H), 6.65-6.70 (1H), 7.41-7.44 (2H), 7.68-7.72 (2H)

Preparation 27

1-Iodo-4-(Pentafluorothio)benzene

To a solution of 4-(pentafluorothio)aniline (15.0 g, 68.4 mmol) and ice (40.0 g) in hydrochloric acid (12M, 30 ml) was added a solution of sodium nitrite (5.0 g, 72.5 mmol) in water (120 ml) at 0° C. After stirring for 2 min, the mixture was added to potassium iodide (13.0 g, 78.3 mmol) in water (120 ml), ensuring the temperature did not rise above 10° C. The reaction mixture was stirred at 0° C. for 10 min and then at room temperature for 60 h. The mixture was extracted with diethyl ether (2×100 ml) and the combined extracts were washed with brine, dried (MgSO$_4$) and concentrated in vacuo. The residue was purified by column chromatography (silica, 300 g), eluting with diethyl ether/cyclohexane [1:10]. The appropriate fractions were combined and concentrated to give the title compound (16.6 g).

$^1$H-NMR (CDCl$_3$): 7.90-7.95 (2H), 8.20-8.25 (2H)

All publications, including but not limited to, issued patents, patent applications, and journal articles, cited in this application are each herein incorporated by reference in their entirety.

Although the invention has been described above with reference to the disclosed embodiments, those skilled in the art will readily appreciate that the specific experiments detailed are only illustrative of the invention. It should be understood that various modifications can be made without departing from the spirit of the invention. Accordingly, the invention is limited only by the following claims.

The invention claimed is:
1. A compound of the formula

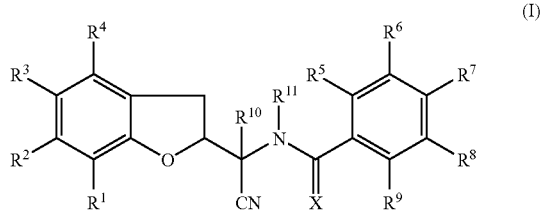

(I)

or a pharmaceutically acceptable salt of said compound, wherein:

X is O or S;

$R^1$, $R^2$, $R^3$ and $R^4$ are each independently selected from H, halo, CN, (C$_1$-C$_4$)alkyl (C$_1$-C$_4$)haloalkyl, O—(C$_1$-C$_4$) alkyl, and O—(C$_1$-C$_4$) haloalkyl;

$R^5$, $R^6$, $R^7$, $R^8$ and $R^9$ are each independently selected from H, halo, (C$_1$-C$_4$)alkyl, (C$_3$-C$_6$)cycloalkyl, (C$_1$-C$_4$)haloalkyl, O—(C$_1$-C$_4$)alkyl, O—(C$_3$-C$_6$)cycloalkyl, O—(C$_1$-C$_4$)haloalkyl, SF$_5$, S(O)$_m$—(C$_1$-C$_4$)alkyl, S(O)$_m$—(C$_3$-C$_6$)cycloalkyl and S(O)$_m$—(C$_1$-C$_4$)haloalkyl;

$R^{10}$ is H or (C$_1$-C$_4$)alkyl;

$R^{11}$ is H or (C$_1$-C$_4$)alkyl;

and m is 0, 1 or 2.

2. A compound according to claim 1 wherein at least one of $R^1$, $R^2$, $R^3$ and $R^4$ is CN and at least two of $R^1$, $R^2$, $R^3$ and $R^4$ are H.

3. A compound according to claim 2 wherein one of $R^1$ and $R^4$ is H and the other is selected from H, F, Cl, Br and CF$_3$, and one of $R^2$ and $R^3$ is H and the other is CN.

4. A compound according to claim 1 wherein one of $R^5$, $R^6$, $R^7$, $R^8$ and $R^9$ is selected from halo, (C$_1$-C$_4$)haloalkyl, O—(C$_1$-C$_4$)haloalkyl, SF$_5$ and S(O)$_m$—(C$_1$-C$_4$)haloalkyl and the others are H.

5. A compound according to claim 4 wherein one of $R^6$ and $R^7$ is CF$_3$, OCF$_3$, SF$_5$, SCF$_3$ or S(O)$_2$CF$_3$, and the other is H.

6. A compound according to claim 5 wherein $R^7$ is CF$_3$, OCF$_3$, SF$_5$, SCF$_3$ or S(O)$_2$CF$_3$ and $R^7$, $R^8$, $R^{10}$ and $R^{11}$ are H.

7. A compound according to claim 1 wherein $R^{10}$ is (C$_1$-C$_4$)alkyl.

8. A compound according to claim 1 wherein $R^{10}$ is methyl.

9. A compound according to claim 1 wherein $R^{11}$ is H.

10. A compound according to claim 1 wherein X is O.

11. A compound according to claim 1 wherein $R^1$ and $R^4$ are each independently selected from H, Cl, Br and CF$_3$, $R^7$ is CF$_3$, OCF$_3$, SF$_5$, SCF$_3$ or S(O)$_2$CF$_3$, and $R^8$ is H.

12. A compound according to claim 11 wherein X is O.

13. A compound according to claim 12 wherein $R^1$ is selected from H, Cl, Br and CF$_3$, $R^2$ is H, $R^3$ is CN, and $R^4$ is H.

14. A compound according to claim 1 selected from:
N-[1-cyano-1-(5-cyano-2,3-dihydro-1-benzofuran-2-yl) ethyl]-4-[(trifluoromethyl)thio]benzamide,
N-{(1R*)-1-cyano-1-[(2R*)-5-cyano-2,3-dihydro-1-benzofuran-2-yl]ethyl}-4-[(trifluoromethyl)thio]benzamide,
N-{(1R)-1-cyano-1-[(2R)-5-cyano-2,3-dihydro-1-benzofuran-2-yl]ethyl}-4-[(trifluoromethyl)thio]benzamide,
N-{(1S)-1-cyano-1-[(2S)-5-cyano-2,3-dihydro-1-benzofuran-2-yl]ethyl}-4-[(trifluoromethyl)thio]benzamide,
N-{(1R*)-1-cyano-1-[(2S*)-5-cyano-2,3-dihydro-1-benzofuran-2-yl]ethyl}-4-[(trifluoromethyl)thio]benzamide,
N-{(1R)-1-cyano-1-[(2S)-5-cyano-2,3-dihydro-1-benzofuran-2-yl]ethyl}-4-[(trifluoromethyl)thio]benzamide,
N-{(1S)-1-cyano-1-[(2R)-5-cyano-2,3-dihydro-1-benzofuran-2-yl]ethyl}-4-[(trifluoromethyl)thio]benzamide,
N-[1-cyano-1-(5-cyano-2,3-dihydro-1-benzofuran-2-yl) ethyl]-4-(trifluoromethoxy)benzamide,
N-{(1R*)-1-cyano-1-[(2R*)-5-cyano-2,3-dihydro-1-benzofuran-2-yl]ethyl}-4-(trifluoromethoxy)benzamide,
N-{(1R)-1-cyano-1-[(2R)-5-cyano-2,3-dihydro-1-benzofuran-2-yl]ethyl}-4-(trifluoromethoxy)benzamide,
N-{(1S)-1-cyano-1-[(2S)-5-cyano-2,3-dihydro-1-benzofuran-2-yl]ethyl}-4-(trifluoromethoxy)benzamide
N-{(1R*)-1-cyano-1-[(2S*)-5-cyano-2,3-dihydro-1-benzofuran-2-yl]ethyl}-4-(trifluoromethoxy)benzamide,
N-{(1R)-1-cyano-1-[(2S)-5-cyano-2,3-dihydro-1-benzofuran-2-yl]ethyl}-4-(trifluoromethoxy)benzamide,
N-{(1S)-1-cyano-1-[(2R)-5-cyano-2,3-dihydro-1-benzofuran-2-yl]ethyl}-4-(trifluoromethoxy)benzamide,
N-[1-(7-chloro-5-cyano-2,3-dihydro-1-benzofuran-2-yl)-1-cyanoethyl]-4-(trifluoromethoxy)benzamide,
N-{(1R*)-1-[(2R*)-7-chloro-5-cyano-2,3-dihydro-1-benzofuran-2-yl)-1-cyanoethyl]-4-(trifluoromethoxy)benzamide,
N-{(1R)-1-[(2R)-7-chloro-5-cyano-2,3-dihydro-1-benzofuran-2-yl)-1-cyanoethyl]-4-(trifluoromethoxy)benzamide, N-{(1S)-1-[(2S)-7-chloro-5-cyano-2,3-dihydro-1-benzofuran-2-yl)-1-cyanoethyl]-4-(trifluoromethoxy)benzamide, N-{(1R*)-1-[(2S*)-7-chloro-5-cyano-2,3-dihydro-1-benzofuran-2-yl)-1-cyanoethyl]-4-(trifluoromethoxy)benzamide, N-{(1R)-1-[(2S)-7-chloro-5-cyano-2,3-dihydro-1-benzofuran-2-yl)-1-cyanoethyl]-4-(trifluoromethoxy)benzamide, N-{(1S)-1-[(2R)-7-chloro-5-cyano-2,3-dihydro-1-benzofuran-2-yl)-1-cyanoethyl]-4-(trifluoromethoxy)benzamide, N-[1-(7-chloro-5-cyano-2,3-dihydro-1-benzofuran-2-yl)-1-cyanoethyl]-4-(pentafluorothio)benzamide, N-{(1R*)-1-[(2R*)-7-chloro-5-cyano-2,3-dihydro-1-benzofuran-2-yl]-1-cyanoethyl]-4-(pentafluorothio)benzamide, N-{(1R)-1-[(2R)-7-chloro-5-cyano-2,3-dihydro-1-benzofuran-2-yl]-1-cyanoethyl]-4-pentafluorothiobenzamide, N-{(1S)-1-[(2S)-7-chloro-5-cyano-2,3-dihydro-1-benzofuran-2-yl]-1-cyanoethyl]-4-(pentafluorothio)benzamide, N-{(1R*)-1-[(2S*)-7-chloro-5-cyano-2,3-dihydro-1-benzofuran-2-yl]-1-cyanoethyl]-4-(pentafluorothio)benzamide, N-{(1R)-1-[(2S)-7-chloro-5-cyano-2,3-dihydro-1-benzofuran-2-yl]-1-cyanoethyl]-4-(pentafluorothio)benzamide, and N-{(1S)-1-[(2R)-7-chloro-5-cyano-2,3-dihydro-1-benzofuran-2-yl]-1-cyanoethyl]-4-(pentafluorothio)benzamide, or a pharmaceutically acceptable salt thereof.

15. A method of treatment of a parasitic infestation in a host animal, comprising treating said host animal with an effective amount of a compound as defined in claim 1 or a pharmaceutically acceptable salt thereof.

16. The method according to claim 15 wherein the host animal is a non-human animal.

17. The method according to claim 15 wherein the parasite is a nematode.

18. A pharmaceutical composition comprising a compound according to claim 1, or a pharmaceutically acceptable salt thereof, and a pharmaceutically acceptable carrier.

19. The pharmaceutical composition according to claim 18 further comprising a second therapeutic agent.

20. The pharmaceutical composition according to claim 19 wherein the second therapeutic agent is selected from ivermectin, avermectin, abamectin, emamectin, eprinomectin, doramectin, selamectin, moxidectin, nemadectin and milbemycin oxime.

21. The pharmaceutical composition according to claim 19 wherein the second therapeutic agent is selected from albendazole, cambendazole, fenbendazole, flubendazole, mebendazole, oxfendazole, oxibendazole and parbendazole.

22. The pharmaceutical composition according to claim 19 wherein the second therapeutic agent is selected from tetramisole, levamisole, pyrantel pamoate, oxantel and morantel.

23. The pharmaceutical composition according to claim 19 wherein the second therapeutic agent is selected from closantel, triclabendazole, clorsulon, rafoxanide, niclosamide, praziquantel and epsiprantel.

24. The pharmaceutical composition according to claim 19 wherein the second therapeutic agent is selected from fipronil, lufenuron, tebufenozide, spinosad and imidacloprid.

* * * * *